(12) United States Patent
Hershfield et al.

(10) Patent No.: US 7,056,713 B1
(45) Date of Patent: Jun. 6, 2006

(54) URATE OXIDASE

(75) Inventors: Michael Hershfield, Durham, NC (US); Susan J. Kelly, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/762,097

(22) PCT Filed: Aug. 5, 1999

(86) PCT No.: PCT/US99/17678

§ 371 (c)(1),
(2), (4) Date: Aug. 23, 2001

(87) PCT Pub. No.: WO00/08196

PCT Pub. Date: Feb. 17, 2000

Related U.S. Application Data

(60) Provisional application No. 60/095,489, filed on Aug. 6, 1998.

(51) Int. Cl.
C12N 9/02 (2006.01)
C12N 15/53 (2006.01)

(52) U.S. Cl. ............... 435/189; 435/252.3; 435/320.1; 536/23.2

(58) Field of Classification Search ............... 435/189, 435/320.1, 252.3; 536/23.2
See application file for complete search history.

(56) References Cited

U.S. PATENT DOCUMENTS

| | | | |
|---|---|---|---|
| 3,613,231 A | 10/1971 | Bergmeyer et al. | 195/66 |
| 4,179,337 A | 12/1979 | Davis et al. | 435/181 |
| 4,460,683 A | 7/1984 | Gloger et al. | 435/10 |
| 4,766,106 A | 8/1988 | Katre et al. | 514/12 |
| 4,847,325 A | 7/1989 | Shadle et al. | 525/54.1 |
| 4,917,888 A * | 4/1990 | Katre et al. | 424/78.3 |
| 5,286,637 A | 2/1994 | Veronese et al. | 435/183 |
| 5,382,518 A | 1/1995 | Caput et al. | 435/191 |
| 5,428,128 A | 6/1995 | Mensi-Fattohi et al. | 530/302 |
| 5,541,098 A | 7/1996 | Caput et al. | 435/191 |
| 5,612,460 A | 3/1997 | Zalipsky | 530/391.9 |
| 5,643,575 A | 7/1997 | Martinez et al. | 424/194.1 |
| 5,653,974 A | 8/1997 | Hung et al. | 424/85.1 |
| 5,880,255 A | 3/1999 | Delgado et al. | 530/303 |
| 5,919,455 A | 7/1999 | Greenwald et al. | 424/178.1 |
| 6,201,110 B1 | 3/2001 | Olsen et al. | 530/402 |
| 6,245,901 B1 | 6/2001 | von der Osten | 530/402 |
| 6,576,235 B1 | 6/2003 | Williams et al. | 424/94.4 |

FOREIGN PATENT DOCUMENTS

| | | |
|---|---|---|
| DE | 279 486 A1 | 6/1990 |
| JP | 09154581 | 6/1997 |
| WO | WO 94/19007 | 9/1994 |
| WO | WO 00/07629 A2 | 2/2000 |
| WO | WO 01/59078 A2 | 8/2001 |

OTHER PUBLICATIONS

Miura, S., et al. (1994) Eur. J. Biochem. 223, 141-146.*
Hershfield, M.S., et al. (1991) Proc. Natl. Acad. Sci., USA 68, 7185-7189.*
Chen, R.H.L., et al. (1981) Biochim. Biophys. Acta 660, 293-298.*
Ito, M., et al. (1992) Biochem. Biophys. Res. Comm. 187 (1), 101-107.*
Yeldandi, A.V., et al. (1990) Biochem. Biophys. Res. Comm. 171 (2), 641-646.*
Wu, X., et al. (1989) Proc. Natl. Acad. Sci., USA 86, 9412-9416.*
Wu, X., et al. (1992) J. Mol. Evol. 34, 78-84.*
Conley, T.G., et al. (1980) Biochem. J. 187, 727-732.*
Henney, C.S., et al. (1968) New Eng. J. Med. 178(21), 1144-1146.*
Hershfield, M.S., et al. (1991) Proc. Natl. Acad. Sci., USA 88, 7185-7189.*
Chua et al, "Use of polyethylene glycol-modified uricase (PEG-uricase) to treat hyperuricemia in a patient with non-Hodgkin lymphoma", Annals of Internal Medicine, New York, NY; Jul. 15, 1988, pp. 114-117.
Davis et al, "Hypouricaemic Effects of Polyethyleneglycol Modified Urate Oxidase" Lancet The, Lancet Limited, London, GB, Aug. 8, 1981, pp. 281-283.
Savoca, K.V., et al., "Induction of Tolerance in Mice by Uricase and Monomethoxypolyethylene Glycol-Modified Uricase," Int. Archs. Allergy Appl. Immunol. 75: 58-67, S. Karger Medical and Scientific Publishers (1984).
Suzuki, H., and Verma, D.P.S., "Soybean Nodule-Specific Uricase (Nodulin-35) Is Expressed and Assembled into a Functional Tetrameric Holoenzyme in *Escherichia coli*," Plant Physiol. 95: 384-389, American Society of Plant Physiologists (1991).
Alvares, K., et al., "Rat urate oxidate produced by recombinant baculovirus expression: Formation of peroxisome crytalloid core-like structure," Proc. Natl. Acad. Sci. USA 89: 4908-4912 (1992).
Calicet, P., et al., "Biopharmaceutical Properties of Uricases Conjugated to Neutral and Amphiphilic Polymers," Bioconj. Chem. 10: 638-646 (Jun. 1999).
Kelly, S.J., et al., "Diabetes Insipidus in Uricase-Deficient Mice: A model for Evaluating Therapy with Poly (Ethylene Glycol) -Modified Uricase," J. Am. Soc. Nephrol. 12: 1001-1009 (2001).
Mountain View Pharmaceuticals, Inc., "PURICASE®," U.S. Trademark Registration No. 2,246,623 (report obtained from U.S. Trademark Electronic Search System (TESS), (Apr. 15, 2003).

(Continued)

*Primary Examiner*—Charles L. Patterson, Jr.
(74) *Attorney, Agent, or Firm*—Nixon & Vanderhye P.C.

(57) ABSTRACT

The present invention relates, in general, to urate oxidase (uricase) proteins and nucleic acid molecules encoding same. In particular, the invention relates to uricase proteins which are particularly useful as, for example, intermediates for making improved modified uricase proteins with reduced immunogenicity and increased bioavailability.

10 Claims, 18 Drawing Sheets

OTHER PUBLICATIONS

R&D Focus Drug News (DataStar File IPNR/IPNA), Accession No. 1998:2984 DRUGNL, "PEG-uricase BioTechnology General, Duke University, Mountain View licensing agreement," (Aug. 24, 1998).

Abuchowski, A., et al., "Effect of Covalent Attachment of Polyethylene Glycol on Immunogenicity and Circulating Life of Bovine Liver Catalase", Journal of Biological Chemistry 252: 3582-3586 (1977).

Burnham, N., "Polymers for Delivering Peptides and Proteins", American Journal of Hospital Pharmacy,51: 210-218 (1994).

Davis, F.F., et al., "Enzyme-Polyethylene Glycol Adducts; Modified Enzymes with Unique Properites", Enzyme Engineering 4: 169-173 (1978).

Fuertges, F., et al., "The Clinical Efficacy of Poly(Ethylene Glycol)-Modified Proteins," J. Controlled Release, 11: 139-148 (1990).

Braun, A., and Alsenz, J., "Development and Use of Enzyme-Linked Immunosorbent Assays (ELISA) for the Detection of Protein Aggregates in Interferon-Alpha (IFN-α) Formulations," Pharm. Res. 14: 1394-1400 (Oct. 1997).

Braun, A., et al., "Protein Aggregates Seem to Play a Key Role Among the Parameters Ingluencing the Antigenicity of Interferon Alpha (IFN-α) in Normal and Transgenic Mice," Pharm. Res. 14: 1472-1478 (Oct. 1997).

Colloc'h, N., et al., "Crystal Structure of the protein drug urate oxidase-inhibitor complex at 2.05 Å resolution," Nature Struct. Biol. 4: 947-952 (Nov. 1997).

Kito, M., et al., "A Simple and Efficient Method for Preparation of Monomethoxypolyethylene Glycol Activated with p-Nitrophenylchloroformate and Its Application to Modification of L-Asparaginase," J. Clin. Biochem. Nutr. 21: 101-111 (1996).

Kunitani, M., et al., "Classical light scattering quantitation of protein aggregates: off-line spectroscopy versus HPLC detection," J. Pharm. Biomed. Anal. 16: 573-586 (Dec. 1997).

Lee, C.C., et al., "Generation of cDNA Probes Directed by Amino Acid Sequence: Cloning of Urate Oxidase," Science 239: 1288-1291 (1988).

Mahler, H.R., et al., "Studies on Uricase: I. Preparation, Purification, and Properties of a Cuproprotein," J. Biol. Chem. 216: 625-641 (1955).

Montalbini, P., et al., "Uricase from leaves: its purification and characterization from three different higher plants," Planta 202: 277-283 (Jul. 1997).

Moore, W.V., and Leppert, P., "Role of Aggregated Human Growth Hormone (hGH) in Development of Antibodies to hGH," J. Clin. Endocrinol. Metab. 51: 691-697 (1980).

Osman, A.M., et al., "Liver Uricase in Camelus dromedarius: Purification and Properties," Comp. Biochem. Physiol 94B: 469-474 (1989).

Palleroni, A.V., et al., "Interferon Immunogenicity: Preclinical Evaluation of Interferon-α2a," J. Interferon Cytokine Res. 17 (Suppl 1): S23-S27 (Jul. 1997).

Porstmann, B., et al., "Comparison of Chromogens for the Determination of Horseradish Peroxidase as a Marker in Enzyme Immunoassay," J. Clin. Chem. Clin. Biochem. 19: 435-439 (1981).

Fam, A.G., "Strategies and Controversies in the Treatment of Gout and Hyperuricaemia," Clinical Rheumatology International Practice and Research 4: 177-192 (1990).

Hande, K.R., et al., "Severe Allupurinol Toxicity," American Journal of Medicine 76: 47-56 (1984).

Hedlund, L.W., et al., "Magnetic Resonance Microscopy of Toxic Renal Injury Induced by Bromoethylamine in Rats," Fundamental and Applied Toxicology 16: 787-797 (1991).

Kahn, K., et al., "Kinetic Mechanism and Cofactor Content of Soybean Root Nodule Urate Oxidase," Biochemistry 36: 4731-4738 (1997).

Kunitani, M., et al., "On-Line Characterization of Polyethylene Glycol-Modified Proteins," Journal of Chromatography 588: 125-137 (1991).

Leach, M., et al., "Efficacy of Urate Oxidase (Uricozyme) in Tumor Lysis Induced Urate Nephropathy," Clinical and Laboratory Haematology 20: 169-172 (1998).

Legoux, R., et al., "Cloning and Expression in *Escherichia coli* of the Gene Encoding *Aspergillus flavus* Urate Oxidase," Journal of Biological Chemistry 267: 8565-8570 (1992).

Mahmoud, H.H., et al., "Advances in the Management of Malignancy-Associated Hyperuricaemia," British Journal of Cancer 77 (Supplement 4): 18-20 (1998).

Nishimura, H., et al., "Improved Modification of Yeast Uricase with Polyethylene Glycol, Accompanied with Nonimmunoreactivity towards Anti-Uricase Serum and High Enzymic Activity," Enzyme 26: 49-53 (1981).

Nucci, M.L., et al., "The Therapeutic Value of Poly(Ethylene Glycol)-Modified Proteins," Advanced Drug Delivery Reviews 6: 133-151 (1991).

Pui, C.H., et al., "Urate Oxidase in Prevention and Treatment of Hyperuricemia Associated with Lymphoid Malignancies," Leukemia 11: 1813-1816 (1997).

Saifer, M., et al., "Plasma Clearence and Immunologic Properties of Long-Acting Superoxide Dismutase Prepared Using 35, 000 to 120,000 Dalton Poly-Ethylene Glycol," Advances in Experimental Medicine and Biology 366: 377-387 (1994).

Sartore, L., et al., "Enzyme Modification by mPEG with an Amino Acid or Peptide as Spacer Arms," Applied Biochemistry and Biotechnology 27: 55-63 (1991).

Shearwater Polymers, Inc., "Functionalized Biochompatible Polymer for Research and Pharmaceuticals," Shearwater Polymers, Inc. Catalog, pp. 27, 47 and 48 (1997-1998).

Venkataseshan, M.A., et al., "Acute Hyperuricemic Nephropathy and Renal Failure after Transplantation," Nephron 56: 317-321 (1990).

Veronese, F.M., et al., "Surface Modification of Proteins," Applied Biochemistry and Biotechnology 11: 141-152 (1985).

Veronese, F.M., et al., "New Synthetic Polymers for Enzyme and Liposome Modification" in *Poly(ethylene Glycol)Chemistry and Biological Applications*, ACS Symposium Series 680, American Chemistry Society, Washington, DC, pp. 182-192 (1997).

Wu, X., et al., "Hyperuricemia and Urate Nephropathy in Urate Oxidase-Deficient Mice," Proceedings of the National Academy of Sciences USA 91: 742-746 (1994).

Yasuda, Y., et al., "Biochemical and Biopharmaceutical Properties of Macromolecular Conjugates of Uricase with Dextran and Polyethylene Glycol," Chemical and Pharmaceutical Bulletin 38: 2053-2056 (1990).

Donadio et al., "Manifestation de Type Anaphylactique après Injection Intra-Veineuse D'urate-Oxydase Chez Un Enfant Asthmatique Atteint De Leucémie Aiguë," La Nouvelle Presse Médicale 10: 711-712 (1981).

Donadio et al., "Manifestation de Type Anaphylactique après Injection Intra-Veineuse D'urate-Oxydase Chez Un Enfant Asthmatique Atteint De Leucémie Aiguë," La Nouvelle Presse Médicale 10: 711-712 (1981). (English Translation).

* cited by examiner

Fig. 5

Deduced Amino Acid Sequences of Pig-Baboon Chimeric Uricase (PBC Uricase)
and Porcine Uricase Containing the Mutations R291K and T301S (PKS Uricase),
Compared with the Porcine and Baboon Sequences

| Porcine | MAHYRNDYKK | NDEVEFVRTG | YGKDMIKVLH | IQRDGKYHSI | 40 |
|---|---|---|---|---|---|
| PBC | 1-225 porcine sequence | → | | | |
| | | | | | |
| PKS | 1-288 porcine sequence | → | | | |
| Baboon | MADYHNNYKK | NDELEFVRTG | YGKDMVKVLH | IQRDGKYHSI | 40 |
| Porcine | KEVATSVQLT | LSSKKDYLHG | DNSDVIPTDT | IKNTVNVLAK | 80 |
| PBC | porcine sequence → | | | | |
| | | | | | |
| PKS | porcine sequence → | | | | |
| Baboon | KEVATSVQLT | LSSKKDYLHG | DNSDIIPTDT | IKNTVHVLAK | 80 |
| Porcine | FKGIKSIETF | AVTICEHFLS | SFKHVIRAQV | YVEEVPWKRF | 120 |
| PBC | porcine sequence → | | | | |
| | | | | | |
| PKS | porcine sequence → | | | | |
| Baboon | FKGIKSIEAF | GVNICEYFLS | SFNHVIRAQV | YVEEIPWKRL | 120 |
| Porcine | EKNGVKHVHA | FIYTPTGTHF | CEVEQIRNGP | PVIHSGIKDL | 160 |
| PBC | porcine sequence → | | | | |
| | | | | | |
| PKS | porcine sequence → | | | | |
| Baboon | EKNGVKHVHA | FIHTPTGTHF | CEVEQLRSGP | PVIHSGIKDL | 160 |
| Porcine | KVLKTTQSGF | EGFIKDQFTT | LPEVKDRCFA | TQVYCKWRYH | 200 |
| PBC | porcine sequence → | | | | |
| | | | | | |
| PKS | porcine sequence → | | | | |
| Baboon | KVLKTTQSGF | EGFIKDQFTT | LPEVKDRCFA | TQVYCKWRYH | 200 |
| Porcine | QGRDVDFEAT | WDTVRSIVLQ | KFAGPYDKGE | YSPSVQKTLY | 240 |
| PBC | porcine sequence | | → \| ← baboon sequence | | |
| | | | | | |
| PKS | porcine sequence → | | | | |
| Baboon | QCRDVDFEAT | WGTIRDLVLE | KFAGPYDKGE | YSPSVQKTLY | 240 |
| Porcine | DIQVLTLGQV | PEIEDMEISL | PNIHYLNIDM | SKMGLINKEE | 280 |
| PBC | baboon sequence → | | | | |
| | | | | | |
| PKS | porcine sequence → | | | | |
| Baboon | DIQVLSLSRV | PEIEDMEISL | PNIHYFNIDM | SKMGLINKEE | 280 |
| Porcine | VLLPLDNPYG | RITGTVKRKL | TSRL | | |
| PBC | baboon sequence → | | 304 | | |
| | | | | | |
| PKS | porcine \| ← baboon | 289-304 | | | |
| Baboon | VLLPLDNPYG | RITGTVKRKL | SSRL | | |

Fig. 6

Comparison of amino acid sequences "stripped-down" version of chimera, known as "PigKS" (also called "Pig-Lys") vs. Pig uricase "Pig KS" uricase:
Pig cDNA from 1 to 864 (NdeI site) and then Baboon 865 to 915 (end)

Pig uricase:
Pig cDNA from 1 to 915 (end)

[GCG GAP program]

```
Gap Weight:        12       Average Match:     2.912
    Length Weight:  4       Average Mismatch: -2.003

Quality: 1601          Length:     319
            Ratio: 5.249           Gaps:       0
Percent Similarity: 99.672   Percent Identity: 99.344

Match display thresholds for the alignment(s):
                  | = IDENTITY
                  : = 2
                  . = 1
``` pigKS.pep x Pig.pep        June 25, 1998 17:11  ..

```
pigKS  1 MAHYRNDYKKNDEVEFVRTGYGKDMIKVLHIQRDGKYHSIKEVATSVQLT 50
         ||||||||||||||||||||||||||||||||||||||||||||||||||
Pig    1 MAHYRNDYKKNDEVEFVRTGYGKDMIKVLHIQRDGKYHSIKEVATSVQLT 50

51 LSSKKDYLHGDNSDVIPTDTIKNTVNVLAKFKGIKSIETFAVTICEHFLS 100
         ||||||||||||||||||||||||||||||||||||||||||||||||||
      51 LSSKKDYLHGDNSDVIPTDTIKNTVNVLAKFKGIKSIETFAVTICEHFLS 100

101 SFKHVIRAQVYVEEVPWKRFEKNGVKHVHAFIYTPTGTHFCEVEQIRNGP 150
         ||||||||||||||||||||||||||||||||||||||||||||||||||
     101 SFKHVIRAQVYVEEVPWKRFEKNGVKHVHAFIYTPTGTHFCEVEQIRNGP 150

151 PVIHSGIKDLKVLKTTQSGFEGFIKDQFTTLPEVKDRCFATQVYCKWRYH 200
         ||||||||||||||||||||||||||||||||||||||||||||||||||
     151 PVIHSGIKDLKVLKTTQSGFEGFIKDQFTTLPEVKDRCFATQVYCKWRYH 200

201 QGRDVDFEATWDTVRSIVLQKFAGPYDKGEYSPSVQKTLYDIQVLTLGQV 250
         ||||||||||||||||||||||||||||||||||||||||||||||||||
     201 QGRDVDFEATWDTVRSIVLQKFAGPYDKGEYSPSVQKTLYDIQVLTLGQV 250

251 PEIEDMEISLPNIHYLNIDMSKMGLINKEEVLLPLDNPYGKITGTVKRKL 300
         |||||||||||||||||||||||||||||||||||||||||:||||||||
     251 PEIEDMEISLPNIHYLNIDMSKMGLINKEEVLLPLDNPYGRITGTVKRKL 300

301 SSRL* 305
         .||||
     301 TSRL*. 305
```

Fig. 7

Comparison of amino acid sequences of the "original" Pig-baboon chimeric uricase ("chimera") with that of the "stripped-down" version of chimera, known as "PigKS" (also called "Pig-Lys")

"Chimera" uricase:
Pig cDNA from 1 to 674 (Apa site) and then Baboon cDNA from 675 to 915 (end)

"Pig KS" uricase:
Pig cDNA from 1 to 864 (NdeI site) and then Baboon 865 to 915 (end)

[GCG GAP program]
```
      Gap Weight:       12        Average Match:     2.912
   Length Weight:        4        Average Mismatch: -2.003

Quality:     1589              Length:       319
           Ratio:     5.210                Gaps:         0
Percent Similarity:  98.689     Percent Identity:    98.689
```

Match display thresholds for the alignment(s):
```
                    | = IDENTITY
                    : = 2
                    . = 1
``` chimera.pep x pigKS.pep    June 25, 1998 16:15  ..

```
chim.    1 MAHYRNDYKKNDEVEFVRTGYGKDMIKVLHIQRDGKYHSIKEVATSVQLT  50
           |||||||||||||||||||||||||||||||||||||||||||||||||||
PigKS    1 MAHYRNDYKKNDEVEFVRTGYGKDMIKVLHIQRDGKYHSIKEVATSVQLT  50

51 LSSKKDYLHGDNSDVIPTDTIKNTVNVLAKFKGIKSIETFAVTICEHFLS 100
           |||||||||||||||||||||||||||||||||||||||||||||||||||
        51 LSSKKDYLHGDNSDVIPTDTIKNTVNVLAKFKGIKSIETFAVTICEHFLS 100

101 SFKHVIRAQVYVEEVPWKRFEKNGVKHVHAFIYTPTGTHFCEVEQIRNGP 150
           |||||||||||||||||||||||||||||||||||||||||||||||||||
       101 SFKHVIRAQVYVEEVPWKRFEKNGVKHVHAFIYTPTGTHFCEVEQIRNGP 150

151 PVIHSGIKDLKVLKTTQSGFEGFIKDQFTTLPEVKDRCFATQVYCKWRYH 200
           |||||||||||||||||||||||||||||||||||||||||||||||||||
       151 PVIHSGIKDLKVLKTTQSGFEGFIKDQFTTLPEVKDRCFATQVYCKWRYH 200

201 QGRDVDFEATWDTVRSIVLQKFAGPYDKGEYSPSVQKTLYDIQVLSLSRV 250
           ||||||||||||||||||||||||||||||||||||||||||||.| .|
       201 QGRDVDFEATWDTVRSIVLQKFAGPYDKGEYSPSVQKTLYDIQVLTLGQV 250

251 PEIEDMEISLPNIHYFNIDMSKMGLINKEEVLLPLDNPYGKITGTVKRKL 300
           ||||||||||||||||| |||||||||||||||||||||||||||||||
       251 PEIEDMEISLPNIHYLNIDMSKMGLINKEEVLLPLDNPYGKITGTVKRKL 300

301 SSRL*. 305
           |||||
       301 SSRL*  305
```

Fig. 8

Comparison of amino acid sequences of the "original" Pig-baboon chimeric uricase ("chimera") with that of Pig uricase "Chimera" uricase:
Pig cDNA from 1 to 674 (Apa site) and then Baboon cDNA from 675 to 915 (end)

Pig uricase:
Pig cDNA from 1 to 915 (end)

[GCG GAP program]
Gap Weight:       12       Average Match:    2.912
    Length Weight:     4   Average Mismatch: -2.003

Quality:  1583          Length:    305
             Ratio:  5.190           Gaps:      0
Percent Similarity: 98.361  Percent Identity: 98.033

Match display thresholds for the alignment(s):
                       | = IDENTITY
                       : = 2
                       . = 1 chimera.pep x Pig.pep     June 25, 1998 16:54

```
chim   1 MAHYRNDYKKNDEVEFVRTGYGKDMIKVLHIQRDGKYHSIKEVATSVQLT  50
         ||||||||||||||||||||||||||||||||||||||||||||||||||
Pig    1 MAHYRNDYKKNDEVEFVRTGYGKDMIKVLHIQRDGKYHSIKEVATSVQLT  50

51 LSSKKDYLHGDNSDVIPTDTIKNTVNVLAKFKGIKSIETFAVTICEHFLS 100
         ||||||||||||||||||||||||||||||||||||||||||||||||||
      51 LSSKKDYLHGDNSDVIPTDTIKNTVNVLAKFKGIKSIETFAVTICEHFLS 100

101 SFKHVIRAQVYVEEVPWKRFEKNGVKHVHAFIYTPTGTHFCEVEQIRNGP 150
         ||||||||||||||||||||||||||||||||||||||||||||||||||
     101 SFKHVIRAQVYVEEVPWKRFEKNGVKHVHAFIYTPTGTHFCEVEQIRNGP 150

151 PVIHSGIKDLKVLKTTQSGFEGFIKDQFTTLPEVKDRCFATQVYCKWRYH 200
         ||||||||||||||||||||||||||||||||||||||||||||||||||
     151 PVIHSGIKDLKVLKTTQSGFEGFIKDQFTTLPEVKDRCFATQVYCKWRYH 200

201 QGRDVDFEATWDTVRSIVLQKFAGPYDKGEYSPSVQKTLYDIQVLSLSRV 250
         |||||||||||||||||||||||||||||||||||||||||||||.| .|
     201 QGRDVDFEATWDTVRSIVLQKFAGPYDKGEYSPSVQKTLYDIQVLTLGQV 250

251 PEIEDMEISLPNIHYFNIDMSKMGLINKEEVLLPLDNPYGKITGTVKRKL 300
         ||||||||||||||||| ||||||||||||||||||||||:|||||||||
     251 PEIEDMEISLPNIHYLNIDMSKMGLINKEEVLLPLDNPYGRITGTVKRKL 300

301 SSRL* 305
         .||||
     301 TSRL* 305
```

Fig. 9

Comparison of amino acid sequence of the "original" Pig-baboon chimeric uricase ("chimera") with that of "Baboon D3H" uricase (Baboon except for His replacing Asp at amino acid 3)

Pig uricase:
Pig cDNA from 1 to 915 (end)

"Baboon D3H" uricase:
"Baboon D3H" cDNA from 1 to 915 (end)

[GCG GAP program]

```
        Gap Weight:     12        Average Match:     2.912
     Length Weight:      4     Average Mismatch:    -2.003

Quality:   1493              Length:       305
              Ratio:  4.895                Gaps:         0
 Percent Similarity: 94.098     Percent Identity:    90.820

Match display thresholds for the alignment(s):
                    | = IDENTITY
                    : = 2
                    . = 1
```

Pig.pep x baboon D3H.pep         June 25, 1998 17:44

```
Pig    1 MAHYRNDYKKNDEVEFVRTGYGKDMIKVLHIQRDGKYHSIKEVATSVQLT 50
         |||| |·||||||·||||||||||||:||||||||||||||||||||||||
Bab    1 MAHYHNNYKKNDELEFVRTGYGKDMVKVLHIQRDGKYHSIKEVATSVQLT 50

51 LSSKKDYLHGDNSDVIPTDTIKNTVNVLAKFKGIKSIETFAVTICEHFLS 100
         ||||||||||||||:|||||||||||·|||||||||||| | |||:|||
      51 LSSKKDYLHGDNSDIIPTDTIKNTVHVLAKFKGIKSIEAFGVNICEYFLS 100

101 SFKHVIRAQVYVEEVPWKRFEKNGVKHVHAFIYTPTGTHFCEVEQIRNGP 150
         || ||||||||||:|||| |||||||||||||:||||||||||||:|·||
     101 SFNHVIRAQVYVEEIPWKRLEKNGVKHVHAFIHTPTGTHFCEVEQLRSGP 150

151 PVIHSGIKDLKVLKTTQSGFEGFIKDQFTTLPEVKDRCFATQVYCKWRYH 200
         |||||||||||||||||||||||||||||||||||||||||||||||||
     151 PVIHSGIKDLKVLKTTQSGFEGFIKDQFTTLPEVKDRCFATQVYCKWRYH 200

201 QGRDVDFEATWDTVRSIVLQKFAGPYDKGEYSPSVQKTLYDIQVLTLGQV 250
         | |||||||| |:| :||:|||||||||||||||||||||||||·| ·|
     201 QCRDVDFEATWGTIRDLVLEKFAGPYDKGEYSPSVQKTLYDIQVLSLSRV 250

251 PEIEDMEISLPNIHYLNIDMSKMGLINKEEVLLPLDNPYGRITGTVKRKL 300
         |||||||||||||||| ||||||||||||||||||||||||:|||||||
     251 PEIEDMEISLPNIHYFNIDMSKMGLINKEEVLLPLDNPYGKITGTVKRKL 300

301 TSRL* 305
         ·||||
     301 SSRL* 305
```

Fig. 10

Comparison of amino acid sequence of the "original" Pig-baboon chimeric uricase ("chimera") with that of "Baboon D3H" uricase (Baboon except for His replacing Asp at amino acid 3)

"Chimera" uricase:
Pig cDNA from 1 to 674 (Apa site) and then Baboon cDNA from 675 to 915 (end)

"Baboon D3H" uricase:
"Baboon D3H" cDNA from 1 to 915 (end)

[GCG GAP program]
```
        Gap Weight:    12       Average Match:    2.912
     Length Weight:     4       Average Mismatch: -2.003

Quality:  1516             Length:      305
             Ratio:  4.970              Gaps:        0
 Percent Similarity: 95.738   Percent Identity:  92.787

Match display thresholds for the alignment(s):
                     | = IDENTITY
                     : = 2
                     . = 1 chimera.pep x baboon D3H.pep      June 25, 1998  17:18
```

```
chim   1 MAHYRNDYKKNDEVEFVRTGYGKDMIKVLHIQRDGKYHSIKEVATSVQLT  50
         ||||  |||||||| ||||||||||||| ||||||||||||||||||||||
Bab    1 MAHYHNNYKKNDELEFVRTGYGKDMVKVLHIQRDGKYHSIKEVATSVQLT  50

51 LSSKKDYLHGDNSDVIPTDTIKNTVNVLAKFKGIKSIETFAVTICEHFLS 100
         ||||||||||||||:|||||||||| |||||||||||||  |  |||:|||
      51 LSSKKDYLHGDNSDIIPTDTIKNTVHVLAKFKGIKSIEAFGVNICEYFLS 100

101 SFKHVIRAQVYVEEVPWKRFEKNGVKHVHAFIYTPTGTHFCEVEQIRNGP 150
         ||  ||||||||||:||||  ||||||||||||||:||||||||||||:|.||
     101 SFNHVIRAQVYVEEIPWKRLEKNGVKHVHAFIHTPTGTHFCEVEQLRSGP 150

151 PVIHSGIKDLKVLKTTQSGFEGFIKDQFTTLPEVKDRCFATQVYCKWRYH 200
         |||||||||||||||||||||||||||||||||||||||||||||||||
     151 PVIHSGIKDLKVLKTTQSGFEGFIKDQFTTLPEVKDRCFATQVYCKWRYH 200

201 QGRDVDFEATWDTVRSIVLQKFAGPYDKGEYSPSVQKTLYDIQVLSLSRV 250
         | |||||||||| :| :||:|||||||||||||||||||||||||||||
     201 QCRDVDFEATWGTIRDLVLEKFAGPYDKGEYSPSVQKTLYDIQVLSLSRV 250

251 PEIEDMEISLPNIHYFNIDMSKMGLINKEEVLLPLDNPYGKITGTVKRKL 300
         |||||||||||||||||||||||||||||||||||||||||||||||||
     251 PEIEDMEISLPNIHYFNIDMSKMGLINKEEVLLPLDNPYGKITGTVKRKL 300

301 SSRL* 305
         |||||
     301 SSRL* 305
```

Fig. 11-1

Bestfit (GCG software) comparison of coding sequences of the cDNAs of Pig KS uricase ("PKS") vs. pig uricase <u>"Pig KS" uricase:</u>
Pig cDNA from 1 to 864 (NdeI site) and then Baboon 865 to 915 (end)

```
        Gap Weight:      50      Average Match:    10.000
     Length Weight:       3      Average Mismatch: -9.000

Quality:    9036             Length:     915
              Ratio:   9.875               Gaps:       0
 Percent Similarity:  99.344    Percent Identity:  99.344

Match display thresholds for the alignment(s):
                      | = IDENTITY
                      : = 5
                      . = 1 pigKS.seq x pig.seq July 25, 1998 10:14  ..
```

```
PKS     1 ATGGCTCATTACCGTAATGACTACAAAAAGAATGATGAGGTAGAGTTTGT 50
          ||||||||||||||||||||||||||||||||||||||||||||||||||
pig     1 ATGGCTCATTACCGTAATGACTACAAAAAGAATGATGAGGTAGAGTTTGT 50

51 CCGAACTGGCTATGGGAAGGATATGATAAAAGTTCTCCATATTCAGCGAG 100
          ||||||||||||||||||||||||||||||||||||||||||||||||||
       51 CCGAACTGGCTATGGGAAGGATATGATAAAAGTTCTCCATATTCAGCGAG 100

101 ATGGAAAATATCACAGCATTAAAGAGGTGGCAACTTCAGTGCAACTGACT 150
          ||||||||||||||||||||||||||||||||||||||||||||||||||
      101 ATGGAAAATATCACAGCATTAAAGAGGTGGCAACTTCAGTGCAACTGACT 150

151 TTGAGCTCCAAAAAAGATTACCTGCATGGAGACAATTCAGATGTCATCCC 200
          ||||||||||||||||||||||||||||||||||||||||||||||||||
      151 TTGAGCTCCAAAAAAGATTACCTGCATGGAGACAATTCAGATGTCATCCC 200

201 TACAGACACCATCAAGAACACAGTTAATGTCCTGGCGAAGTTCAAAGGCA 250
          ||||||||||||||||||||||||||||||||||||||||||||||||||
      201 TACAGACACCATCAAGAACACAGTTAATGTCCTGGCGAAGTTCAAAGGCA 250

251 TCAAAAGCATAGAAACTTTTGCTGTGACTATCTGTGAGCATTTCCTTTCT 300
          ||||||||||||||||||||||||||||||||||||||||||||||||||
      251 TCAAAAGCATAGAAACTTTTGCTGTGACTATCTGTGAGCATTTCCTTTCT 300

301 TCCTTCAAGCATGTCATCAGAGCTCAAGTCTATGTGGAAGAAGTTCCTTG 350
          ||||||||||||||||||||||||||||||||||||||||||||||||||
      301 TCCTTCAAGCATGTCATCAGAGCTCAAGTCTATGTGGAAGAAGTTCCTTG 350

351 GAAGCGTTTTGAAAAGAATGGAGTTAAGCATGTCCATGCATTTATTTATA 400
          ||||||||||||||||||||||||||||||||||||||||||||||||||
      351 GAAGCGTTTTGAAAAGAATGGAGTTAAGCATGTCCATGCATTTATTTATA 400
```

Fig. 11-2

```
401 CTCCTACTGGAACGCACTTCTGTGAGGTTGAACAGATAAGGAATGGACCT 450
    ||||||||||||||||||||||||||||||||||||||||||||||||||
401 CTCCTACTGGAACGCACTTCTGTGAGGTTGAACAGATAAGGAATGGACCT 450

451 CCAGTCATTCATTCTGGAATCAAAGACCTAAAAGTCTTGAAAACAACCCA 500
    ||||||||||||||||||||||||||||||||||||||||||||||||||
451 CCAGTCATTCATTCTGGAATCAAAGACCTAAAAGTCTTGAAAACAACCCA 500

501 GTCTGGCTTTGAAGGATTCATCAAGGACCAGTTCACCACCCTCCCTGAGG 550
    ||||||||||||||||||||||||||||||||||||||||||||||||||
501 GTCTGGCTTTGAAGGATTCATCAAGGACCAGTTCACCACCCTCCCTGAGG 550

551 TGAAGGACCGGTGCTTTGCCACCCAAGTGTACTGCAAATGGCGCTACCAC 600
    ||||||||||||||||||||||||||||||||||||||||||||||||||
551 TGAAGGACCGGTGCTTTGCCACCCAAGTGTACTGCAAATGGCGCTACCAC 600

601 CAGGGCAGAGATGTGGACTTTGAGGCCACCTGGGACACTGTTAGGAGCAT 650
    ||||||||||||||||||||||||||||||||||||||||||||||||||
601 CAGGGCAGAGATGTGGACTTTGAGGCCACCTGGGACACTGTTAGGAGCAT 650

651 TGTCCTGCAGAAATTTGCTGGGCCCTATGACAAAGGCGAGTACTCGCCCT 700
    ||||||||||||||||||||||||||||||||||||||||||||||||||
651 TGTCCTGCAGAAATTTGCTGGGCCCTATGACAAAGGCGAGTACTCGCCCT 700

701 CTGTCCAGAAGACACTCTATGACATCCAGGTGCTCACCCTGGGCCAGGTT 750
    ||||||||||||||||||||||||||||||||||||||||||||||||||
701 CTGTCCAGAAGACACTCTATGACATCCAGGTGCTCACCCTGGGCCAGGTT 750

751 CCTGAGATAGAAGATATGGAAATCAGCCTGCCAAATATTCACTACTTAAA 800
    ||||||||||||||||||||||||||||||||||||||||||||||||||
751 CCTGAGATAGAAGATATGGAAATCAGCCTGCCAAATATTCACTACTTAAA 800

801 CATAGACATGTCCAAAATGGGACTGATCAACAAGGAAGAGGTCTTGCTAC 850
    ||||||||||||||||||||||||||||||||||||||||||||||||||
801 CATAGACATGTCCAAAATGGGACTGATCAACAAGGAAGAGGTCTTGCTAC 850

851 CTTTAGACAATCCATATGGAAAAATTACTGGTACAGTCAAGAGGAAGTTG 900
    |||||||||||||||||||| | |||||||||||||||||||||||| ||
851 CTTTAGACAATCCATATGGCAGGATTACTGGTACAGTCAAGAGGAAGCTG 900

901 TCTTCAAGACTGTGA 915
    |||||||| ||||||
901 ACTTCAAGGCTGTGA 915
```

Fig. 12-1

Bestfit (GCG software) comparison of coding sequences of the cDNAs of Pig KS uricase ("PKS") vs. baboon uricase "Pig KS" uricase:
Pig cDNA from 1 to 864 (NdeI site) and then Baboon 865 to 915 (end)

```
         Gap Weight:    50       Average Match:  10.000
      Length Weight:     3    Average Mismatch:  -9.000

Quality:  7573            Length:    915
               Ratio: 8.277              Gaps:      0
  Percent Similarity: 90.929  Percent Identity: 90.929

Match display thresholds for the alignment(s):
                  | = IDENTITY
                  : = 5
                  . = 1
``` pigKS.seq x baboon.seq July 25, 1998 10:21 ..

```
PKS    1 ATGGCTCATTACCGTAATGACTACAAAAAGAATGATGAGGTAGAGTTTGT  50
         ||||| | |||| |||  |||| ||||||||||||||| | ||||||||
bab    1 ATGGCCGACTACCATAACAACTATAAAAAGAATGATGAATTGGAGTTTGT  50

51 CCGAACTGGCTATGGGAAGGATATGATAAAAGTTCTCCATATTCAGCGAG 100
         |||||||||||||||||||||||||| |||||||||||||||||||||||
      51 CCGAACTGGCTATGGGAAGGATATGGTAAAAGTTCTCCATATTCAGCGAG 100

101 ATGGAAAATATCACAGCATTAAAGAGGTGGCAACTTCAGTGCAACTGACT 150
         |||||||||||||||||||||||||||||||||||||||||||||| ||
     101 ATGGAAAATATCACAGCATTAAAGAGGTGGCAACTTCAGTGCAACTTACT 150

151 TTGAGCTCCAAAAAAGATTACCTGCATGGAGACAATTCAGATGTCATCCC 200
         ||||  ||||||||||||||||||||||||||||| ||||| |||||||
     151 CTGAGTTCCAAAAAAGATTACCTGCATGGAGATAATTCAGATATCATCCC 200

201 TACAGACACCATCAAGAACACAGTTAATGTCCTGGCGAAGTTCAAAGGCA 250
         ||||||||||||||||||||||||| ||||| |||||| |||| || ||
     201 TACAGACACCATCAAGAACACAGTTCATGTCTTGGCAAAGTTTAAGGGAA 250

251 TCAAAAGCATAGAAACTTTTGCTGTGACTATCTGTGAGCATTTCCTTTCT 300
         |||||||||||||| |  |||| |||||   |||||| |||| ||||||
     251 TCAAAAGCATAGAAGCCTTTGGTGTGAATATTTGTGAGTATTTTCTTTCT 300

301 TCCTTCAAGCATGTCATCAGAGCTCAAGTCTATGTGGAAGAAGTTCCTTG 350
         || || || |||||  ||| |||||||||||| ||||||||| ||||||
     301 TCTTTTAACCATGTAATCCGAGCTCAAGTCTACGTGGAAGAAATCCCTTG 350

351 GAAGCGTTTTGAAAAGAATGGAGTTAAGCATGTCCATGCATTTATTTATA 400
         ||||||| |||||||||||||||||||||||||||||||||||||| |
     351 GAAGCGTCTTGAAAAGAATGGAGTTAAGCATGTCCATGCATTTATTCACA 400
```

Fig. 12-2

```
401 CTCCTACTGGAACGCACTTCTGTGAGGTTGAACAGATAAGGAATGGACCT 450
    ||||  ||||||||| |||||||||||| ||||||||  | || | ||||||
401 CTCCCACTGGAACACACTTCTGTGAAGTTGAACAACTGAGAAGTGGACCC 450

451 CCAGTCATTCATTCTGGAATCAAAGACCTAAAAGTCTTGAAAACAACCCA 500
    || |||||||||||||||||||||||||||| || |||||||||||||| ||
451 CCCGTCATTCATTCTGGAATCAAAGACCTCAAGGTCTTGAAAACAACACA 500

501 GTCTGGCTTTGAAGGATTCATCAAGGACCAGTTCACCACCCTCCCTGAGG 550
    ||||||  |||||||  ||||||||||||||||||||||||||||||||||
501 GTCTGGATTTGAAGGTTTCATCAAGGACCAGTTCACCACCCTCCCTGAGG 550

551 TGAAGGACCGGTGCTTTGCCACCCAAGTGTACTGCAAATGGCGCTACCAC 600
    |||||||||| ||||||||||||||||||||||||||| |||||||||||
551 TGAAGGACCGATGCTTTGCCACCCAAGTGTACTGCAAGTGGCGCTACCAC 600

601 CAGGGCAGAGATGTGGACTTTGAGGCCACCTGGGACACTGTTAGGAGCAT 650
    ||| ||||| ||||||||||| |||||| ||||||| ||  ||  || | |
601 CAGTGCAGGGATGTGGACTTCGAGGCTACCTGGGGCACCATTCGGGACCT 650

651 TGTCCTGCAGAAATTTGCTGGGCCCTATGACAAAGGCGAGTACTCGCCCT 700
    ||||||| ||||||||||||||||||||||||||||||||||||||| |||
651 TGTCCTGGAGAAATTTGCTGGGCCCTATGACAAAGGCGAGTACTCACCCT 700

701 CTGTCCAGAAGACACTCTATGACATCCAGGTGCTCACCCTGGGCCAGGTT 750
    |||| ||||||||| ||||||| |||||||||||| ||||| ||| |||
701 CTGTGCAGAAGACCCTCTATGATATCCAGGTGCTCTCCCTGAGCCAGTT 750

751 CCTGAGATAGAAGATATGGAAATCAGCCTGCCAAATATTCACTACTTAAA 800
    ||||||||||||||||||||||||||||||||||||| |||||||||| ||
751 CCTGAGATAGAAGATATGGAAATCAGCCTGCCAAACATTCACTACTTCAA 800

801 CATAGACATGTCCAAAATGGGACTGATCAACAAGGAAGAGGTCTTGCTAC 850
    | ||||||||||||||||||| |||||||||||||||||||||||||||  |
801 TATAGACATGTCCAAAATGGGTCTGATCAACAAGGAAGAGGTCTTGCTGC 850

851 CTTTAGACAATCCATATGGAAAAATTACTGGTACAGTCAAGAGGAAGTTG 900
    | ||||||||||||||||||||||||||||||||||||||||||||||||||
851 CATTAGACAATCCATATGGAAAAATTACTGGTACAGTCAAGAGGAAGTTG 900

901 TCTTCAAGACTGTGA 915
    |||||||||||||||
901 TCTTCAAGACTGTGA 915
```

Fig. 13-1

Bestfit (GCG software) comparison of coding sequences of the cDNAs of "original" pig-baboon chimeric uricase ("PBC") vs. pig uricase "PBC" uricase:
Pig cDNA from 1 to 674 (Apa site) then Baboon cDNA from 675 to 915 (end). PBC chimeric cDNA can be cut out with NcoI plus BamHI

```
         Gap Weight:     50      Average Match:    10.000
      Length Weight:      3      Average Mismatch: -9.000

Quality:   8770             Length:      915
               Ratio:  9.585               Gaps:        0
  Percent Similarity: 97.814    Percent Identity:   97.814

Match display thresholds for the alignment(s):
                      | = IDENTITY
                      : = 5
                      . = 1

PBC.seq x pig.seq        July 25, 1998 08:10  ..
```

```
PBC    1 ATGGCTCATTACCGTAATGACTACAAAAAGAATGATGAGGTAGAGTTTGT 50
         ||||||||||||||||||||||||||||||||||||||||||||||||||
PIG    1 ATGGCTCATTACCGTAATGACTACAAAAAGAATGATGAGGTAGAGTTTGT 50

51 CCGAACTGGCTATGGGAAGGATATGATAAAAGTTCTCCATATTCAGCGAG 100
         ||||||||||||||||||||||||||||||||||||||||||||||||||
      51 CCGAACTGGCTATGGGAAGGATATGATAAAAGTTCTCCATATTCAGCGAG 100

101 ATGGAAAATATCACAGCATTAAAGAGGTGGCAACTTCAGTGCAACTGACT 150
         ||||||||||||||||||||||||||||||||||||||||||||||||||
     101 ATGGAAAATATCACAGCATTAAAGAGGTGGCAACTTCAGTGCAACTGACT 150

151 TTGAGCTCCAAAAAAGATTACCTGCATGGAGACAATTCAGATGTCATCCC 200
         ||||||||||||||||||||||||||||||||||||||||||||||||||
     151 TTGAGCTCCAAAAAAGATTACCTGCATGGAGACAATTCAGATGTCATCCC 200

201 TACAGACACCATCAAGAACACAGTTAATGTCCTGGCGAAGTTCAAAGGCA 250
         ||||||||||||||||||||||||||||||||||||||||||||||||||
     201 TACAGACACCATCAAGAACACAGTTAATGTCCTGGCGAAGTTCAAAGGCA 250

251 TCAAAAGCATAGAAACTTTTGCTGTGACTATCTGTGAGCATTTCCTTTCT 300
         ||||||||||||||||||||||||||||||||||||||||||||||||||
     251 TCAAAAGCATAGAAACTTTTGCTGTGACTATCTGTGAGCATTTCCTTTCT 300

301 TCCTTCAAGCATGTCATCAGAGCTCAAGTCTATGTGGAAGAAGTTCCTTG 350
         ||||||||||||||||||||||||||||||||||||||||||||||||||
     301 TCCTTCAAGCATGTCATCAGAGCTCAAGTCTATGTGGAAGAAGTTCCTTG 350

351 GAAGCGTTTTGAAAAGAATGGAGTTAAGCATGTCCATGCATTTATTTATA 400
         ||||||||||||||||||||||||||||||||||||||||||||||||||
     351 GAAGCGTTTTGAAAAGAATGGAGTTAAGCATGTCCATGCATTTATTTATA 400
```

Fig. 13-2

```
401 CTCCTACTGGAACGCACTTCTGTGAGGTTGAACAGATAAGGAATGGACCT 450
    ||||||||||||||||||||||||||||||||||||||||||||||||||
401 CTCCTACTGGAACGCACTTCTGTGAGGTTGAACAGATAAGGAATGGACCT 450

451 CCAGTCATTCATTCTGGAATCAAAGACCTAAAAGTCTTGAAAACAACCCA 500
    ||||||||||||||||||||||||||||||||||||||||||||||||||
451 CCAGTCATTCATTCTGGAATCAAAGACCTAAAAGTCTTGAAAACAACCCA 500

501 GTCTGGCTTTGAAGGATTCATCAAGGACCAGTTCACCACCCTCCCTGAGG 550
    ||||||||||||||||||||||||||||||||||||||||||||||||||
501 GTCTGGCTTTGAAGGATTCATCAAGGACCAGTTCACCACCCTCCCTGAGG 550

551 TGAAGGACCGGTGCTTTGCCACCCAAGTGTACTGCAAATGGCGCTACCAC 600
    ||||||||||||||||||||||||||||||||||||||||||||||||||
551 TGAAGGACCGGTGCTTTGCCACCCAAGTGTACTGCAAATGGCGCTACCAC 600

601 CAGGGCAGAGATGTGGACTTTGAGGCCACCTGGGACACTGTTAGGAGCAT 650
    ||||||||||||||||||||||||||||||||||||||||||||||||||
601 CAGGGCAGAGATGTGGACTTTGAGGCCACCTGGGACACTGTTAGGAGCAT 650

651 TGTCCTGCAGAAATTTGCTGGGCCCTATGACAAAGGCGAGTACTCACCCT 700
    |||||||||||||||||||||||||||||||||||||||||||||  |||
651 TGTCCTGCAGAAATTTGCTGGGCCCTATGACAAAGGCGAGTACTCGCCCT 700

701 CTGTGCAGAAGACCCTCTATGATATCCAGGTGCTCTCCCTGAGCCGAGTT 750
    |||| |||||||||  ||||||||  |||||||||| |||||| ||  ||
701 CTGTCCAGAAGACACTCTATGACATCCAGGTGCTCACCCTGGGCCAGGTT 750

751 CCTGAGATAGAAGATATGGAAATCAGCCTGCCAAACATTCACTACTTCAA 800
    |||||||||||||||||||||||||||||||||||| ||||||||||| |
751 CCTGAGATAGAAGATATGGAAATCAGCCTGCCAAATATTCACTACTTAAA 800

801 TATAGACATGTCCAAAATGGGTCTGATCAACAAGGAAGAGGTCTTGCTGC 850
       ||||||||||||||||||| |||||||||||||||||||||||||| |
801 CATAGACATGTCCAAAATGGGACTGATCAACAAGGAAGAGGTCTTGCTAC 850

851 CATTAGACAATCCATATGGAAAAATTACTGGTACAGTCAAGAGGAAGTTG 900
    | |||||||||||||||||| |||||||||||||||||||||||||| ||
851 CTTTAGACAATCCATATGGCAGGATTACTGGTACAGTCAAGAGGAAGCTG 900

901 TCTTCAAGACTGTGA 915
    |||||||  ||||||
901 ACTTCAAGGCTGTGA 915
```

Fig. 14-1

Bestfit (GCG software) comparison of coding sequences of the cDNAs of "original" pig-baboon chimeric uricase ("PBC") vs. baboon uricase "PBC" uricase:
Pig cDNA from 1 to 674 (Apa site) then Baboon cDNA from 675 to 915 (end). PBC chimeric cDNA can be cut out with NcoI plus BamHI

```
         Gap Weight:      50       Average Match:  10.000
      Length Weight:       3    Average Mismatch:  -9.000

Quality:    7839             Length:     915
              Ratio:   8.567               Gaps:       0
  Percent Similarity: 92.459    Percent Identity:  92.459

Match display thresholds for the alignment(s):
                       | = IDENTITY
                       : = 5
                       . = 1

PBC.seq x Wubaboon.seq         July 25, 1998 09:36  ..
```

```
PBC    1 ATGGCTCATTACCGTAATGACTACAAAAAGAATGATGAGGTAGAGTTTGT 50
         ||||| | |||| ||| |||| |||||||||||||| | ||||||||||
Bab    1 ATGGCCGACTACCATAACAACTATAAAAAGAATGATGAATTGGAGTTTGT 50

51 CCGAACTGGCTATGGGAAGGATATGATAAAAGTTCTCCATATTCAGCGAG 100
         |||||||||||||||||||||||||| ||||||||||||||||||||||
      51 CCGAACTGGCTATGGGAAGGATATGGTAAAAGTTCTCCATATTCAGCGAG 100

101 ATGGAAAATATCACAGCATTAAAGAGGTGGCAACTTCAGTGCAACTGACT 150
         |||||||||||||||||||||||||||||||||||||||||||||| ||
     101 ATGGAAAATATCACAGCATTAAAGAGGTGGCAACTTCAGTGCAACTTACT 150

151 TTGAGCTCCAAAAAAGATTACCTGCATGGAGACAATTCAGATGTCATCCC 200
         |||| ||||||||||||||||||||||||||||  |||||| | |||||
     151 CTGAGTTCCAAAAAAGATTACCTGCATGGAGATAATTCAGATATCATCCC 200

201 TACAGACACCATCAAGAACACAGTTAATGTCCTGGCGAAGTTCAAAGGCA 250
         |||||||||||||||||||||||||| ||||| ||||||||| ||| ||
     201 TACAGACACCATCAAGAACACAGTTCATGTCTTGGCAAAGTTTAAGGGAA 250

251 TCAAAAGCATAGAAACTTTTGCTGTGACTATCTGTGAGCATTTCCTTTCT 300
         |||||||||||| | |||| ||||| ||| ||||| ||||| ||||||
     251 TCAAAAGCATAGAAGCCTTTGGTGTGAATATTTGTGAGTATTTTCTTTCT 300

301 TCCTTCAAGCATGTCATCAGAGCTCAAGTCTATGTGGAAGAAGTTCCTTG 350
         || || || ||||| || ||||||||||||| |||||||||| |||||
     301 TCTTTTAACCATGTAATCCGAGCTCAAGTCTACGTGGAAGAAATCCCTTG 350

351 GAAGCGTTTTGAAAAGAATGGAGTTAAGCATGTCCATGCATTTATTTATA 400
         ||||||| ||||||||||||||||||||||||||||||||||||||| |
     351 GAAGCGTCTTGAAAAGAATGGAGTTAAGCATGTCCATGCATTTATTCACA 400
```

Fig. 14-2

```
401 CTCCTACTGGAACGCACTTCTGTGAGGTTAACAGATAAGGAATGGACCT 450
    ||||  ||||||||| ||||||||||| ||||||||  | || | ||||||
401 CTCCCACTGGAACACACTTCTGTGAAGTTAACAACTGAGAAGTGGACCC 450

451 CCAGTCATTCATTCTGGAATCAAAGACCTAAAAGTCTTGAAAACAACCCA 500
    || |||||||||||||||||||||||||| || |||||||||||||| ||
451 CCCGTCATTCATTCTGGAATCAAAGACCTCAAGGTCTTGAAAACAACACA 500

501 GTCTGGCTTTGAAGGATTCATCAAGGACCAGTTCACCACCCTCCCTGAGG 550
    |||||| ||||||| || ||||||||||||||||||||||||||||||||
501 GTCTGGATTTGAAGGTTTCATCAAGGACCAGTTCACCACCCTCCCTGAGG 550

551 TGAAGGACCGGTGCTTTGCCACCCAAGTGTACTGCAAATGGCGCTACCAC 600
    ||||||||||  ||||||||||||||||||||||||| ||||||||||||
551 TGAAGGACCGATGCTTTGCCACCCAAGTGTACTGCAAGTGGCGCTACCAC 600

601 CAGGGCAGAGATGTGGACTTTGAGGCCACCTGGGACACTGTTAGGAGCAT 650
    ||| |||| ||||||||||| |||||| ||||||  ||| ||| || | |
601 CAGTGCAGGGATGTGGACTTCGAGGCTACCTGGGGCACCATTCGGGACCT 650

651 TGTCCTGCAGAAATTTGCTGGGCCCTATGACAAAGGCGAGTACTCACCCT 700
    ||||||| ||||||||||||||||||||||||||||||||||||||||||
651 TGTCCTGGAGAAATTTGCTGGGCCCTATGACAAAGGCGAGTACTCACCCT 700

701 CTGTGCAGAAGACCCTCTATGATATCCAGGTGCTCTCCCTGAGCCGAGTT 750
    ||||||||||||||||||||||||||||||||||||||||||||||||||
701 CTGTGCAGAAGACCCTCTATGATATCCAGGTGCTCTCCCTGAGCCGAGTT 750

751 CCTGAGATAGAAGATATGGAAATCAGCCTGCCAAACATTCACTACTTCAA 800
    ||||||||||||||||||||||||||||||||||||||||||||||||||
751 CCTGAGATAGAAGATATGGAAATCAGCCTGCCAAACATTCACTACTTCAA 800

801 TATAGACATGTCCAAAATGGGTCTGATCAACAAGGAAGAGGTCTTGCTGC 850
    ||||||||||||||||||||||||||||||||||||||||||||||||||
801 TATAGACATGTCCAAAATGGGTCTGATCAACAAGGAAGAGGTCTTGCTGC 850

851 CATTAGACAATCCATATGGAAAAATTACTGGTACAGTCAAGAGGAAGTTG 900
    ||||||||||||||||||||||||||||||||||||||||||||||||||
851 CATTAGACAATCCATATGGAAAAATTACTGGTACAGTCAAGAGGAAGTTG 900

901 TCTTCAAGACTGTGA 915
    |||||||||||||||
901 TCTTCAAGACTGTGA 915
```

URATE OXIDASE

The present application claims benefit of U.S. Provisional Application No. 60/095,489, filed Aug. 6, 1998, the entire contents of which is incorporated herein by reference.

The present application is a 371 U.S. national phase of PCT/US99/17678, filed 5 Aug. 1999.

The invention disclosed herein was made with U.S. Government support under Grant No. DK48529, awarded by the National Institutes of Health. The Government has certian rights in the invention.

The present invention relates, in general, to urate oxidase (uricase) proteins and nucleic acid molecules encoding same. In particular, the invention relates to uricase proteins which are particularly useful as, for example, intermediates for making improved modified uricase proteins with reduced immunogenicity and increased bioavailability. The preferred modified uricase proteins of the present invention include the uricase proteins covalently bound to poly(ethylene glycols) or poly(ethylene oxides). The present invention provides, therefore, uricase proteins, antibodies which specifically bind with the proteins, nucleic acid molecules enoding the uricase proteins and useful fragments thereof, vectors containing the nucleic acid molecules, host cells containing the vectors and methods of using and making the uricase proteins and nucleic acid molecules.

BACKGROUND

Gout is the most common inflammatory joint disease in men over age 40 (Roubenoff 1990). Painful gouty arthritis occurs when an elevated blood level of uric acid (hyperuricemia) leads to the episodic formation of microscopic crystals of monosodium urate monohydrate in joints. Over time, chronic hyperuricemia can also result in destructive crystalline urate deposits (tophi) around joints, in soft tissues, and in some organs (Hershfield 1996). Uric acid has limited solubility in urine and when overexcreted (hyperuricosuria) can cause kidney stones (uricolithiasis). In patients with certain malignancies, particularly leukemia and lymphoma, marked hyperuricemia and hyperuricosuria (due to enhanced tumor cell turnover and lysis during chemotherapy) pose a serious risk of acute, obstructive renal failure (Sandberg et al. 1956; Gold and Fritz 1957; Cohen et al. 1980; Jones et al. 1990). Severe hyperuricemia and gout are associated with renal dysfunction from various causes, including cyclosporine therapy to prevent organ allograft rejection (West et al. 1987; Venkataseshan et al. 1990; Ahn et al. 1992; Delaney et al. 1992; George and Mandell 1995).

Hyperuricemia can result from both urate overproduction and underexcretion (Hershfield and Seegmiller 1976; Kelley et al. 1989; Becker and Roessler 1995). When mild, hyperuricemia can be controlled with diet, but when pronounced and associated with serious clinical consequences, it requires treatment with drugs, either a uricosuric agent that promotes uric acid excretion (ineffective if renal function is reduced), or the xanthine oxidase inhibitor allopurinol, which blocks urate formation. Allopurinol is the mainstay of therapy in patients with tophaceous gout, renal insufficiency, leukemia, and some inherited disorders. Treatment for hyperuricemia is generally effective and well-tolerated. However, some patients with disfiguring, incapacitating tophaceous gout are refractory to all conventional therapy (Becker 1988; Fam 1990; Rosenthal and Ryan 1995). Moreover, ~2% of patients treated with allopurinol develop allergic reactions, and a severe hypersensitivity syndrome occurs in ~0.4% (Singer and Wallace 1986; Arellano and Sacristan 1993). This often life-threatening syndrome can cause acute renal and hepatic failure, and severe skin injury (toxic epidermal necrolysis, exfoliative dermatitis, erythema multiforme, Stevens-Johnson syndrome). Allopurinol also interferes with the metabolism of azathioprine and 6-mercaptopurine, drugs used in the treatment of leukemia and for prevention of organ allograft rejection, conditions in which marked hyperuricemia occurs and may cause severe gout or threaten renal function.

Ultimately, hyperuricemia is the result of mutational inactivation of the human gene for urate oxidase (uricase) during evoultion (Wu et al. 1989; Wu et al. 1992). Active uricase in liver peroxisomes of most non-human primates and other mammals converts urate to allantoin (+$CO_2$ and $H_2O_2$), which is 80–100 times more soluble than uric acid and is handled more efficiently by the kidney. Parenteral uricase, prepared from *Aspergillus flavus*(Uricozyme®, Clin-Midy, Paris), has been used to treat severe hyperuricemia associated with leukemia chemotherapy for over 20 years in France and Italy (London and Hudson 1957; Kissel et al. 1968; Brogard et al. 1972; Kissel et al. 1972; Potaux et al. 1975; Zittoun et al. 1976; Brogard et al. 1978; Masera et al. 1982), and has been used in recent clinical trials in leukemia patients in the US (Pui et al. 1997). Uricase has a more rapid onset of action than allopurinol (Masera et al. 1982; Pui et al. 1997). In patients with gout, uricase infusions can interrupt acute attacks and decrease the size of tophi (Kissel et al. 1968; Potaux et al. 1975; Brogard et al. 1978).

Though effective for treating acute hyperuricemia during a short course of chemotherapy, daily infusion of *A. flavus* uricase would be a serious drawback for treating recurrent or tophaceous gout. In addition, efficacy of *A. flavus* uricase diminishes quickly in patients who develop anti-uricase antibodies (Kissel et al. 1968; Brogard et al. 1978; Escudier et al. 1984; Mourad et al. 1984; Sibony et al. 1984). Serious allergic reactions, including anaphylaxis, have occurred (Donadio et al. 1981; Montagnac and Schillinger 1990; Pui et al. 1997). A longer-acting, less immunogenic preparation of uricase is clearly needed for chronic therapy.

One approach for sequestering exogenous enzymes from proteases and the immune system involves covalent attachment of the inert, nontoxic polymer, monomethoxypolyethylene glycol (PEG) to the surface of proteins (Harris and Zalipsky 1997). Use of PEGs with Mr ~1,000 to >10,000 was first shown to prolong the circulating life and reduce the immunogenicity of several foreign proteins in animals (Abuchowski et al. 1977a; Abuchowski et al. 1977b; Davis et al. 1981a; Abuchowski et al. 1984; Davis et al. 1991). In 1990, bovine adenosine deaminase (ADA) modified with PEG of Mr 5000 (PEG-ADA, ADAGEN®, produced by Enzon, Inc.) became the first PEGylated protein to be approved by the United States Food and Drug Administration, for treatment of severe combined immune deficiency disease due to ADA deficiency (Hershfield et al. 1987). Experience over the past 12 years has shown that anti-ADA antibodies can be detected by a sensitive ELISA in most patients during chronic treatment with PEG-ADA, but there have been no allergic or hypersensitivity reactions; accelerated clearance of PEG-ADA has occurred in a few anti-ADA antibody producing patients, but this has usually been a transient effect (Chaffee et al. 1992; Hershfield 1997). It should be appreciated that immune function of patients with ADA deficiency usually does not become normal during treatment with PEG-ADA (Hershfield 1995; Hershfield and Mitchell 1995). Thus, immunogenicity might be a more significant problem in developing a PEGylated enzyme for chronic treatment of patients with normal immune function.

Immunogenicity will be understood by one of ordinary skill as relating to the induction of an immune response by an injected preparation of an antigen (such as PEG-modified protein or unmodified protein), while antigenicity refers to the reaction of an antigen with preexisting antibodies. Collectively, antigenicity and immunogenicity are referred to as immunoreactivity. In previous studies of PEG-uricase, immunoreactivity was assessed by a variety of methods, including: the reaction in vitro of PEG-uricase with pre-formed antibodies; measurements of induced antibody synthesis; and accelerated clearance rates after repeated injections.

PEGylation has been shown to reduce the immunogenicity and prolong the circulating life of fungal and porcine uricases in animals (Chen et al. 1981; Savoca et al. 1984; Tsuji et al. 1985; Veronese et al. 1997). PEG-modified *Candida* uricase rapidly lowered serum urate to undetectable levels in 5 normouricemic human volunteers (Davis et al. 1981b). PEGylated *Arthrobacter* uricase produced by Enzon, Inc. was used on a compassionate basis to treat an allopurinol-hypersensitive patient with lymphoma, who presented with renal failure and marked hyperuricemia (Chua et al. 1988; Greenberg and Hershfield 1989). Four intramuscular injections were administered over about two weeks. During this brief period, hyperuricemia was controlled and no anti-uricase antibody could be detected by ELISA in the patient's plasma. Further use and clinical development of this preparation has not been pursued.

To date, no form of uricase or PEG-uricase has been developed that has a suitably long circulating life and sufficiently reduced immunogenicity for safe and reliable use in chronic therapy. The aim of this invention is to provide an improved form of uricase that, in combination with PEGylation, can meet these requirements. The invention is a unique recombinant uricase of mammalian derivation, which has been modified by mutation in a manner that has been shown to enhance the ability of PEGylation to mask potentially immunogenic eptiopes.

SUMMARY OF THE INVENTION

It is a general object of the present invention to provide novel uricase proteins and nucleic acid sequences encoding same.

It is another object of the present invention to provide a method of purifying recombinantly produced uricase proteins, such as those described herein.

It is a further object of the present invention to provide a method of reducing the amount of uric acid in a body fluid of a mammal by administering a composition containing a uricase protein of the present invention to the mammal.

It is yet another object of the present invention to provide antibodies to the uricase proteins described herein.

It is another object of the present invention to provide vectors and host cells containing the nucleic acid sequences described herein and methods of using same to produce the uricase proteins coded by same.

The present invention provides uricase proteins which may be used to produce a substantially non-immunogenic PEG-uricase that retains all or nearly all of the uricolytic activity of the unmodified enzyme. Uricolytic activity is expressed herein in International Units (IU) per mg protein wherein an IU of uricase activity is defined as the amount of enzyme which consumes one micromole of uric acid per minute.

The present invention provides a recombinant uricase protein of a mammalian species which has been modified to insert one or more lysine residues. Recombinant protein, as used herein, refers to any artificially produced protein and is distinguished from naturally produced proteins (i.e., that are produced in tissues of an animal that possesses only the natural gene for the specific protein of interest). Protein includes peptides and amino acid sequences. The recombinant uricase protein of the present invention may be a chimera or hybrid of two or more mammalian proteins, peptides or amino acid sequences. In one embodiment, the present invention can be used to prepare a recombinant uricase protein of a mammalian species, which protein has been modified to increase the number of lysines to the point where, after PEGylation of the recombinant uricase protein, the PEGylated uricase product is substantially as enzymatically active as the unmodifed uricase and the PEGylated uricase product is not unacceptably immunogenic. Truncated forms of the uricases of the present invention are also contemplated wherein amino and/or carboxy terminal ends of the uricase may not be present. Preferably, the uricase is not truncated to the extent that lysines are removed.

One of ordinary skill will appreciate that the conjugated uricase-carrier complex must not contain so many linkages as to substantially reduce the enzymatic activity of the uricase or too few linkages so as to remain unacceptably immunogenic. Preferably, the conjugate will retain at least about 70% to about 90% of the uricolytic activity of the unmodified uricase protein while being more stable, such that it retains its enzymatic activity on storage, in mammalian plasma and/or serum at physiological temperature, as compared to the unmodified uricase protein. Retention of at least about 80% to about 85% of the uricolytic activity would be acceptable. Moreover, in a preferred embodiment, the conjugate provides a substantially reduced immunogenicity and/or immunoreactivity than the unmodified uricase protein. In one embodiment, the present invention provides a uricase protein described herein which can be modified by attachment to a non-toxic, non-immunogenic, pharmaceutically acceptable carrier, such as PEG, by covalent linkage to at least 1 of the lysines contained in the uricase protein. Alternatively, the uricase protein is modified by covalent attachment to a carrier through less than about 10 lysines of its amino acid sequence. Attachment to any of 2, 3, 4, 5, 6, 7, 8, or 9 of the lysines are contemplated as alternative embodiments.

The uricase protein of the present invention is a recombinant molecule which includes segments of porcine and baboon liver uricase proteins. A modified baboon sequence is also provided. In one embodiment, the present invention provides a chimeric pig-baboon uricase (PBC uricase (SEQ ID NO:2)) which includes amino acids (aa) 1–225 of porcine uricase (SEQ ID NO:7) and aa 226–304 of baboon uricase (SEQ ID NO:6) (see also sequence in FIG. 5). In another embodiment, the present invention provides a chimeric pig-baboon uricase (PKS uricase) which includes aa 1–288 of porcine uricase and aa 289–304 of baboon uricase (SEQ ID NO: 4). Truncated derivates of PBC and PKS are also contemplated. Preferred truncated forms are PBC and PKS proteins truncated to delete either the 6 amino terminal amino acids or the 3 carboxy terminal amino acids, or both. Representative sequences are given in SEQ ID NO:s 8 (PBC amino truncated), 9 (PBC carboxy truncated), 10 (PKS amino truncated) and 11 (PKS carboxy truncated). Each of the PBC uricase, PKS uricase and their truncated forms have one to four more lysines than are found in other mammalian uricases that have been cloned.

The present invention provides nucleic acid (DNA and RNA) molecules (sequences), including isolated, purified and/or cloned forms of the nucleic acid molecules, which code for the uricase proteins and truncated proteins described herein. Preferred embodiments are shown in SEQ ID NO:1 (PBC uricase) and SEQ ID NO:3 (PKS uricase).

Vectors (expression and cloning) including these nucleic acid molecules are also provided by the present invention.

Moreover, the present invention provides host cells containing these vectors.

Antibodies which specifically bind to the uricase proteins of the present invention are also provided. Antibodies to the amino portion to the pig uricase and antibodies to the carboxy portion of baboon uricase, when used in conjunction, should be useful in detecting PBC, or other similar chimeric proteins. Preferably, the antibody to the amino portion of the chimeric uricase should not recognize the amino portion of the baboon uricase and similarly, the antibody to the carboxy portion of the chimeric uricase should not recognize the carboxy portion of the pig uricase. More preferably, antibodies are provided which specifically bind PBC or PKS but do not bind the native proteins, such as pig and/or baboon uricases.

In another embodiment, the present invention can be used to prepare a pharmaceutical composition for reducing the amount of uric acid in body fluids, such as urine and/or serum or plasma, containing at least one of the uricase proteins or uricase conjugates described herein and a pharmaceutically acceptable carrier, diluent or excipient.

The present invention also may be used in a method for reducing the amount of uric acid in body fluids of a mammal. The method includes administering to a mammal an uric acid-lowering effective amount of a composition containing a uricase protein or uricase conjugate of the present invention and a diluent, carrier or excipient, which is preferably a pharmaceutically acceptable carrier, diluent or excipient. The mammal to be treated is preferably a human.

The administering step may be, for example, injection by intravenous, intradermal, subcutaneous, intramuscular or intraperitoneal routes. The elevated uric acid levels may be in blood or urine, and may be associated with gout, tophi, renal insufficiency, organ transplantation or malignant disease.

In another embodiment, the present invention provides a method for isolating and or purifying a uricase from a solution of uricase containing, for example, cellular and subcellular debris from, for example, a recombinant production process. Preferably, the method of purification takes advantage of the limited solubility of mammalian uricase at low pH (Conley et al. 1979), by washing the crude recombinant extract at a pH of about 7 to about 8.5 to remove a majority of the proteins that are soluble at this low pH range, whereafter active uricase is solubilized in a buffer, preferably sodium carbonate buffer, at a pH of about 10–11, preferably about 10.2. The solubilized active uricase may then be applied to an anion exchange column, such as a Q Sepharose column, which is washed with low to high salt gradient in a buffer at a pH of about 8.5, after which purified uricase is obtained by eluting with a sodium chloride gradient in sodium carbonate buffer at a pH of about 10 to about 11, preferably about 10.2. The enzyme may be further purified by gel filtration chromatography at a pH of about 10 to about 11. At this stage, the enzyme may be further purified by lowering the pH to about 8.5 or less to selectively precipitate uricase, but not more soluble contaminates. After washing at low pH (7–8) the uricase is then solubilized at a pH of about 10.2. The uricase preparation could then be analyzed by methods known in the art of pharmaceutical preparation, such as, for example, any one of high performance liquid chromatography (HPLC), other chromatographic methods, light scattering, centrifugation and/or gel electrophoresis.

BRIEF DESCRIPTION OF THE DRAWINGS

FIG. 5 shows the deduced amino acid sequences of pig-baboon chimeric uricase (PBC uricase) (SEQ ID NO:2) and porcine uricase containing the mutations R291K and T301S (PKS uricase) (SEQ ID NO:4), compared with the porcine (SEQ ID NO:7) and baboon (SEQ ID NO:6) sequences.

FIG. 6. Comparison of amino acid sequences PKS (SEQ ID NO:4) and pig (SEQ ID NO:7) uricase.

FIG. 7. Comparison of amino acid sequences of PBC (SEQ ID NO:2) and PKS (SEQ ID NO:4).

FIG. 8. Comparison of amino acid sequences of PBC (SEQ ID NO:2) and pig SEQ ID NO:7) uricase.

FIG. 9. Comparison of amino acid sequence of pig uricase (SEQ ID NO:7) and D3H (SEQ ID NO:5).

FIG. 10. Comparison of amino acid sequences of PBC (SEQ ID NO:2) and D3H (SEQ ID NO:5).

FIGS. 11-1 and 11-2. Bestfit (GCG software) comparison of coding sequences of the cDNAs of PKS (SEQ ID NO:3) and pig (SEQ ID NO:12) uricase.

FIGS. 12-1 and 12-2. Bestfit (GCG software) comparison of coding sequences of the cDNAs of PKS (SEQ ID NO:3) and baboon (SEQ ID NO:13) uricase.

FIGS. 13-1 and 13-2. Bestfit (GCG software) comparison of coding sequences of the cDNAs of PBC (SEQ ID NO:1) and pig (SEQ ID NO:12) uricase.

FIGS. 14-1 and 14-2. Bestfit (GCG software) comparison of coding sequences of the cDNAs of PBC (SEQ ID NO:1) and baboon (SEQ ID NO:13) uricase.

DETAILED DESCRIPTION OF THE INVENTION

Figure 1:
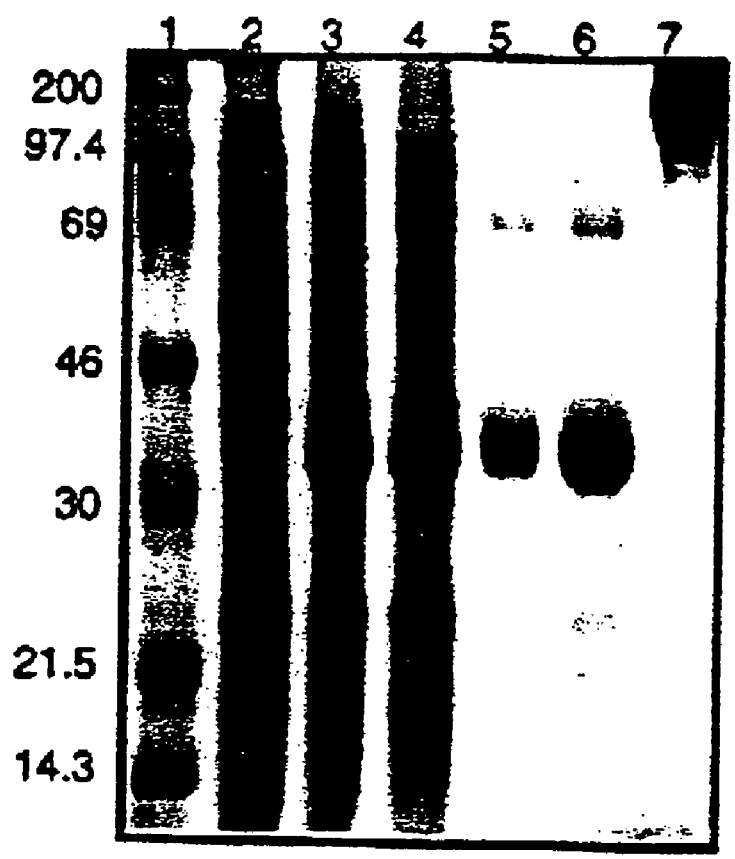
FIG. 1. SDS-mercaptoethanol PAGE (12% gel) analysis

The present invention provides uricase proteins which are useful intermediates for improved uricase conjugates of water-soluble polymers, preferably poly(ethylene glycols) or poly(ethylene oxides), with uricases. Uricase, as used herein, includes individual subunits as well as the native tetramer, unless otherwise indicated.

Although humans do not make an active enzyme, uricase mRNA transcripts have been amplified from human liver RNA (Wu et al. 1992). It is theoretically possible that some human uricase transcripts are translated; even if the peptide products were not full length or were unstable, they could be processed by antigen presenting cells and play a role in determining the immunlogic response to an exogenous uricase used for treatment. It may, in theory, be possible to reconstruct and express a human uricase cDNA by eliminating the two known nonsense mutations. However, in the absence of selective pressure, it is very likely that deleterious missense mutations have accumulated in the human gene during the millions of years since the first nonsense mutation was introduced (Wu et al. 1989; Wu et al. 1992).

Identifying and "correcting" all mutations to obtain maximal catalytic activity and protein stability would be very difficult.

The present inventors have appreciated that there is a high degree of homology (similarity) between the deduced amino acid sequence of human uricase to those of pig (about 86%) and baboon (about 92%) (see, FIGS. 6–14, for example of measure of similarity), whereas homology (similarity) between human and *A. flavus* uricase is <40% (Lee et al. 1988; Reddy et al. 1988; Wu et al. 1989; Legoux et al. 1992; Wu et al. 1992). The present invention provides recombinantly produced chimeric uricase proteins from two different mammals which have been designed to be less immunoreactive to humans than more distantly related fungal or bacterial enzyme. Use of a mammalian uricase derivative is expected to be more acceptable to patients and their physicians.

Experience has shown that activated PEGs such as have been used to make PEG-ADA and to modify other proteins attach via primary amino groups of the amino terminal residue (when present and unblocked) and epsilon-amino groups of lysines. This strategy is useful both because mild reaction conditions can be used, and because positvely charged lysines tend to be located on the surfaces of proteins. The latter is important since for any therapeutic protein the desired effects of PEGylation will depend in part on the characteristics of the PEG polymer (e.g. mass, branched or unbranched stucture, etc.) as well as on the number and distribution of PEG attachment sites of the protein relative to the epitopes and structural elements that determine function and clearance of the protein. A strategy for enhancing the ability of PEGylation to 'mask' epitopes and reduce immunogenicity by semi-selectively introducing novel lysine residues for potential PEG addition has been devised (Hershfield et al. 1991). This strategy employs mutagenesis to replace selected arginine codons with lysine codons, a substitution that maintains positive charge and has minimal effect on computer-predicted indices of surface probability and antigenicity (useful when only amino acid sequence is known).

As an experimental test of this strategy, recombinant *E. coli* purine nucleoside phosphorylase (EPNP) (Hershfield et al. 1991) has been used. Arg-to-Lys substitutions at 3 sites were introduced, increasing the number of lysines per sub-unit from 14 to 17, without altering catalytic activity. The purified triple-mutant retained full activity after modification of ~70% of accessible $NH_2$ groups with excess disuccinyl-PEG5000. Titration of reactive amino groups before and after PEGylation suggested that the triple mutant could accept one more PEG strand per subunit than the wild type enzyme. PEGylation increased the circulating life of both the wild type and mutant EPNP enzymes in mice from ~4 hours to >6 days. After a series of intraperitoneal injections at weekly/biweekly intervals, all mice treated with both unmodified EPNPs, and 10 of 16 mice (60%) injected with PEGylated wild type EPNP, developed high levels of anti-EPNP antibody and a marked decline in circulating life. In contrast, only 2/12 mice (17%) treated with the mutant PEG-EPNP developed rapid clearance; low levels of antibody in these mice did not correlate with circulating life. This strategy was thus successful in substantially reducing immunogenicity even though only 1 of the 3 new lysines became modified after treatment with activated PEG.

The baboon and pig uricase subunits each consist of 304 amino acids, 29 of which (i.e. 1 in about 10 residues) are lysines. Initially attempts to introduce 2 Arg-to-Lys substitutions into the cloned cDNA for baboon uricase, and also a substitution of Lys for a Glu codon at position 208, which is known to be a Lys in the human uricase gene, resulted in an expressed mutant baboon protein which had greatly reduced uricase catalytic activity. It was apparent from this experiment that the ability to maintain uricase enzyme activity after arginine to lysine mutation of the mammalian DNA sequence was not predictable.

Subsequently, it was appreciated that amino acid residue 291 in the baboon uricase is lysine, but the corresponding residue in pig is arginine. The ApaI restriction site present in both cDNAs was exploited to construct a chimeric uricase in which the first 225 amino acids are derived from the pig cDNA and the carboxy terminal 79 are derived from the baboon cDNA. The resulting pig-baboon chimeric (PBC) uricase (SEQ ID NO:2) possesses 30 lysines, one more than either "parental" enzyme. An additional feature of the PBC uricase is that its "baboon" portion differs from human uricase at 4 of 79 amino acid residues, whereas pig and human uricase differ at 10 in the same region. A modified version of PBC was subsequently constructed, which maintains the extra lysine at position 291 and otherwise differs from pig uricase only by a substituion of serine for threonine at residue 301 ("pigKS" uricase (SEQ ID NO:4)). In view of the results described in the preceding paragraph wherein several other insertions of lysines were deleterious to activity, it was unexpected that the PBC and PKS chimeric uricase were fully as active as compared to the unmutated native pig uricase and approximately more than four fold active than unmutated native baboon uricase.

The present invention provides a recombinant pig-baboon chimeric uricase, composed of portions of the pig and baboon liver uricase sequences. One example of such a chimeric uricase contains the first 225 amino acids from the porcine uricase sequence (SEQ ID NO:7) and the last 79 amino acids from the baboon uricase sequence (SEQ ID NO:6) (pig-baboon uricase, or PBC uricase; FIG. 6 and SEQ ID NO:2). Another example of such a chimeric uricase contains the first 288 amino acids from the porcine sequence (SEQ ID NO:7) and the last 16 amino acids from the baboon sequence (SEQ ID NO:6). Since the latter sequence differs from the porcine sequence at only two positions, having a lysine (K) in place of arginine at residue 291 and a serine (S) in place of threonine at residue 301, this mutant is referred to as pig-K-S or PKS uricase.

Vectors (expression and cloning) including the nucleic acid molecules coding the proteins of the present invention are also provided. Preferred vectors include those exemplified herein. One of ordinary skill will appreciate that nucleic acid molecules may be inserted into an expression vector, such as a plasmid, in proper orientation and correct reading frame for expression. If necessary, the nucleic acid (DNA) may be linked to appropriate transcriptional and translational regulatory nucleotide sequences recognized by the desired host, although such control elements are generally available in expression vectors used and known in the art. The vector may then be introduced into the host cells through standard techniques. Generally, not all of the host cells will be transformed by the vector. It may be necessary, therefore, to select transformed host cells. One such selection method known in the art involves incorporating into the expression vector a DNA sequence, with any necessary control elements, which codes for a selectable marker trait in the transformed cell, such as antibiotic resistance. Alternatively, the gene for such a selectable trait may be in another vector which is used to co-transform the desired host cells. The vectors can also include an appropriate promoter, such as a prokaryotic promoter capable of expression (transcripton and translation) of the DNA in a bacterial host cell, such as *E. coli*, transformed therewith. Many expression systems are available and known in the art, including bacterial (for example *E. Coli* and *Bacillus subtilis*), yeasts (for example *Saccharomyces cerevisiae*), filamentous fungi (for example *Aspergillus*), plant cells, animal cells and insect cells.

Suitable vectors may include a prokaryotic replicon, such as ColE1 ori, for propagation in, for example, a prokaryote. Typical prokaryotic vector plasmids are pUC18, pUC19, pUC322 and pBR329 available from Biorad Laboratories (Richmond, Calif.) and pTcr99A and pKK223-3 available from Pharmacia (Piscataway, N.J.). A typical mammalian cell vector plasmid is pSVL available from Pharmacia (Piscataway, N.J.). This vector uses the SV40 late promoter to drive expression of cloned genes, the highest level of expression being found in T antigen-producing cells, such as COS-1 cells. An example of an inducible mammalian expression vector is pMSG, also available from Pharmacia. This vector uses the glucocorticoid-inducible promoter of the mouse mammary tumor virus long terminal repeat to drive expression of the cloned gene. Useful yeast plasmid vectors are pRS403–406 and pRS413–416, and are generally available from Stratagene Cloning Systems (LaJolla, Calif.). Plasmids pRS403, pRS404, pRS405, and pRS406 are Yeast Integrating plasmids (Yips) and incorporate the yeast selectable markers HIS3, TRP1, LEU2 and URA3. Plasmids pRS413–416 are Yeast Centomere plasmids (Ycps).

Moreover, the present invention provides host cells containing these vectors. Preferred host cells include those exemplified and described herein.

The uricase proteins of the present invention may be conjugated via a biologically stable, nontoxic, covalent linkage to a relatively small number of strands of PEG to improve the biological half-life and solubility of the proteins and reduce their immunoreactivity. Such linkages may include urethane (carbamate) linkages, secondary amine linkages, and amide linkages. Various activated PEGs suitable for such conjugation are commercially available from Shearwater Polymers, Huntsville, Ala.

The invention also may be used to prepare pharmaceutical compositions of the uricase proteins as conjugates. These conjugates are substantially non-immunogenic and retain at least 70%, preferably 80%, and more preferably at least about 90% or more of the uricolytic activity of the unmodified enzyme. Water-soluble polymers suitable for use in the present invention include linear and branched poly(ethylene glycols) or poly(ethylene oxides), all commonly known as PEGs. One example of branched PEG is the subject of U.S. Pat. No. 5,643,575.

In one embodiment of the invention, the average number of lysines inserted per uricase subunit is between 1 and 10. In a preferred embodiment, the number of additional lysines per uricase subunit is between 2 and 8. It being understood that the number of additional lysines should not be so many as to be a detriment to the catalytic activity of the uricase. The PEG molecules of the conjugate are preferably conjugated through lysines of the uricase protein, more preferably, through a non-naturally occurring lysine or lysines which have been introduced into the portion of a designed protein which does not naturally contain a lysine at that position.

The present invention provides a method of increasing the available non-deleterious PEG attachment sites to a uricase protein wherein a native uricase protein is mutated in such a manner so as to introduce at least one lysine residue therein. Preferably, this method includes replacement of arginines with lysines.

PEG-uricase conjugates utilizing the present invention are useful for lowering the levels (i.e., reducing the amount) of uric acid in the blood and/or urine of mammals, preferably humans, and can thus be used for treatment of elevated uric acid levels associated with conditions including gout, tophi, renal insufficiency, organ transplantation and malignant disease.

PEG-uricase conjugates may be introduced into a mammal having excessive uric acid levels by any of a number of routes, including oral, by enema or suppository, intravenous, subcutaneous, intradermal, intramuscular and intraperitoneal routes. Patton, J S, et al., (1992) Adv Drug Delivery Rev 8:179–228.

The effective dose of PEG-uricase will depend on the level of uric acid and the size of the individual. In one embodiment of this aspect of the invention, PEG-uricase is administered in a pharmaceutically acceptable excipient or diluent in an amount ranging from 10 μg to about 1 g. In a preferred embodiment, the amount administered is between about 100 μg and 500 mg. More preferably, the conjugated uricase is administered in an amount between 1 mg and 100 mg, such as, for example, 5 mg, 20 mg, or 50 mg. Masses given for dosage amounts of the embodiments refer to the amount of protein in the conjugate.

Pharmaceutical formulations containing PEG-uricase can be prepared by conventional techniques, e.g., as described in Remington's Pharmaceutical Sciences, (1985) Easton, Pa.: Mack Publishing Co. Suitable excipients for the preparation of injectable solutions include, for example, phosphate buffered saline, lactated Ringer's solution, water, polyols and glycerol. Pharmaceutical compositions for parenteral injection comprise pharmaceutically acceptable sterile aqueous or non-aqueous liquids, dispersions, suspensions, or emulsions as well as sterile powders for reconstitution into sterile injectable solutions or dispersions just prior to use. These formulations can contain additional components, such as, for example, preservatives, solubilizers, stabilizers, wetting agents, emulsifiers, buffers, antioxidants and diluents.

PEG-uricase may also be provided as controlled release compositions for implantation into an individual to continually control elevated uric acid levels in blood and urine. For example, polylactic acid, polyglycolic acid, regenerated collagen, poly-L-lysine, sodium alginate, gellan gum, chitosan, agarose, multi lamellar liposomes and many other conventional depot formulations comprise bioerodible or biodegradable materials that can be formulated with biologically active compositions. These materials, when implanted or injected, gradually break down and release the active material to the surrounding tissue. For example, one method of encapsulating PEG-uricase comprises the method disclosed in U.S. Pat. No. 5,653,974, which is hereby incorporated by reference. The use of bioerodible, biodegradable and other depot formulations is expressly contemplated in the present invention. The use of infusion pumps and matrix entrapment systems for delivery of PEG-uricase is also within the scope of the present invention. PEG-uricase may also advantageously be enclosed in micelles or liposomes. Liposome encapsulation technology is well known in the art. See, e.g., Lasic, D, et al., (Eds.) (1995) Stealth Liposomes, Boca Raton, Fla.: CRC Press.

The PEG-uricase pharmaceutical compositions described herein will decrease the need for hemodialysis in patients at high risk of urate-induced renal failure, e.g., organ transplant recipients (see Venkataseshan, V S, et al., (1990) Nephron 56:317–321) and patients with some malignant diseases. In patients with large accumulations of crystalline urate (tophi), such pharmaceutical compositions will improve the quality of life more rapidly than currently available treatments.

The following examples, which are not to be construed as limiting the invention in any way, illustrate the various aspects disclosed above.

EXAMPLE 1

A. Construction of PBC, PKS and Related Uricase cDNAs.

Standard methods, and where applicable instructions supplied by the manufacturers of reagents, were used for preparing total cellular RNA, for PCR amplification (U.S. Pat. Nos. 4,683,195 and 4,683,202, 4,965,188 & 5,075,216) of urate oxidase cDNAs, and for cloning and sequencing of these cDNAs (Erlich 1989; Sambrook et al. 1989; Ausubel 1998). PCR primers for pig and baboon urate oxidases (Table 1) were designed based on published coding sequences (Wu et al. 1989) and using the PRIME software program (Genetics Computer Group, Inc.).

TABLE 1

Primers for PCR Amplification of Urate Oxidase cDNA

Pig liver uricase cDNA:

sense: 5' gcgcgaattccATGGCTCATTACCGTAATGACTACA 3'.
Antisense: 5' gcgctctagaagcttccatggTCACAGCCTTGAAGTCAGC 3'.
D3H baboon liver uricase cDNA:

sense: 5' gcgcgaattccATGGCCCACTACCATAACAACTAT 3'
antisense: 5' gcgcccatggtctagaTCACAGTCTTGAAGACAACTTCCT Restriction enzyme sequences (lowercase) introduced at the ends of the primers are sense (pig and baboon) EcoRI and NcoI; antisense (pig) NcoI, HindIII, XbaI; antisense (baboon) NcoI. In the case of baboon sense primer, the third codon GAC (Aspartate) present in baboon urate oxidase (Wu et al. 1992) was replaced with CAC (Histidine), the codon that is present at this position in the coding sequence of the human urate oxidase pseudogene (Wu et al. 1992). For this reason the recombinant baboon urate oxidase generated from the use of these primers has been named D3H baboon urate oxidase.

Total cellular RNA from pig and baboon livers was reverse-transcribed using a 1st strand kit (Pharmacia Biotech Inc. Piscataway, N.J.). PCR amplification using Taq DNA polymerase (GibcoBRL, Life Technologies, Gaithersburg, Md.) was performed in a thermal cycler (Ericomp, San Diego, Calif.) with the program [30 s, 95° C.; 30 s, 55°; 60 S, 70°], 20 cycles, followed by [30 s, 95° C.; 60 s, 70°] 10 cycles. The urate oxidase PCR products were digested with EcoRI and HindIII and cloned into pUC18 (pig), and were also cloned directly (pig and D3H baboon) using the TA cloning system (Invitrogen, Carlsbad, Calif.). cDNA clones were transformed into the *E. coli* strain XL1-Blue (Stratagene, La Jolla, Calif.). Plasmid DNA containing cloned uricase cDNAs was prepared and the cDNA insert sequence was analyzed by standard dideoxy technique. Clones that possessed the published urate oxidase DNA coding sequences (except for the D3H substitution in baboon urate oxidase described in Table I) were constructed and verified in a series of subsequent steps by standard recombinant DNA methodology.

The pig and D3H baboon cDNAs containing full length coding sequences were introduced into pET expression vectors (Novagen, Madison, Wis.) as follows. The D3H baboon uricase cDNA was excised from the TA plasmid with the NcoI and BamHI restriction enzymes and then subcloned into the NcoI and BamHI cloning sites of the expression plasmids pET3d and pET9d. Full length pig uricase cDNA was excised from a pUC plasmid clone with the EcoRI and HindIII restriction enzymes and subcloned into the EcoRI and HindIII sites of pET28b. The pig cDNA coding region was also introduced into the NcoI and BlpI sites of the expression plasmid pET9d after excision from the NcoI and BlpI sites of pET28b.

The pig-baboon chimera (PBC) cDNA was constructed by excising the 624 bp NcoI-ApaI restriciton fragment of D3H baboon uricase cDNA from a pET3d-D3H-baboon clone, and then replacing this D3H baboon segment with the corresponding 624 bp NcoI-ApaI restriciton fragment of pig cDNA. The resulting PBC urate oxidase cDNA consists of the pig urate oxidase codons 1–225 joined in-frame to codons 226–304 of baboon urate oxidase.

The pig-KS urate oxidase (PigKS) cDNA was constructed by excising the 864 bp NcoI-NdeI restriciton fragment of D3H baboon uricase cDNA from a pET3d-D3H baboon clone, and then replacing this D3H baboon segment with the corresponding 864 bp NcoI-NdeI restriciton fragment of pig cDNA. The resulting PKS urate oxidase cDNA consists of the pig urate oxidase codons 1–288 joined in-frame to codons 289–304 of baboon urate oxidase.

The amino acid sequences of the D3H baboon, pig, PBC, and PKS urate oxidases are shown in FIG. 5 and the SEQUENCE LISTING). Standard techniques were used to prepare 15% glycerol stocks of each of these transformants, and these were stored at −70° C. When each of these species was expressed and the recombinant enzymes isolated (Table 2), the pig, PBC chimera, and PigKS uricases had very similar specific activity, which was approximately 4–5 fold higher than the specific activity of recombinant baboon uricase. This order was confirmed in several other experiments. The specific activity of PBC uricase prepared by several different procedures varied over a 2–2.5-fold range.

TABLE 2

Comparison of Expressed Recombinant Mammalian Uricases

| Construct | Specific Activity* (Units/mg) | Relative Activity (Chimera = 1) |
|---|---|---|
| PBC | 7.02 | 1.00 |
| PigKS | 7.17 | 1.02 |
| Pig | 5.57 | 0.79 |
| Baboon | 1.36 | 0.19 |

*Protein was determined by the Lowry method.
Uricase activity was determined spectrophotometrically (Priest and Pitts 1972).
The assay was carried out at 23–25° C. in a 1 cm quartz cuvette containing a 1 ml reaction mixture (0.1M sodium borate, pH 8.6, 0.1 mM uric acid).
Uric acid disappearance was monitored by decrease in absorbance at 292 nm.
One international unit (IU) of uricase catalyzes the disappearance of one μmol of uric acid per minute.

*E. coli* BL21(DE3)pLysS transformants of the 4 uricase cDNA-pET constructs indicated in Table 2 were plated on LB agar containing selective antibiotics (carbenicillin and chloramphenicol for pET3d (pigKS); kanamycin and chloramphenicol for pET9d (PBC, pig, baboon)), as directed in the pET System Manual (Novagen, Madison Wis.). 5-ml cultures (LB plus antibiotics) were innoculated with single tranformant colonies and grown for 3 hours at 37° C. Then 0.1 ml aliquots were transferred to 100 ml of LB medium containing selective antibiotics and 0.1% lactose (to induce uricase expression). After overnight growth at 37°, bacterial cells from 0.5 ml aliquots of the cultures were extracted into SDS-PAGE loading buffer, and analyzed by SDS-mercaptoethanol PAGE: this established that comparable levels of uricase protein had been expressed in each of the 4 cultures (results not shown). The remaining cells from each 100 ml culture were harvested by centrifugation and washed in PBS. The cells were then re-suspended in 25 ml of phosphate-buffered saline, pH 7.4 (PBS) containing 1 mM AEBSF protease inhibitor (Calbiochem, San Diego, Calif.) and then lysed on ice in a Bacterial Cell Disruptor (Microfluidics, Boston Mass.). The insoluble material (including uricase) was pelleted by centrifugation (20,190×g, 4°, 15 min). The pellets were washed twice with 10 ml of PBS, and then were extracted overnight at 4° with 2 ml of 1 M $Na_2CO_3$, pH 10.2. The extracts were diluted to 10 ml with water and then centrifuged (20,190×g, 4°, 15 min). Uricase activity and protein concentrations were then determined.

EXAMPLE 2

Expression and Isolation of Recombinant PBC Uricase (4 Liter Fermentor Prep).

The pET3d-PBC uricase transformant was plated from a glycerol stock onto an LB agar plate containing carbenicillin and chloramphenicol, as directed in the Novagen pET System Manual. A 200 ml inoculum started from a single colony was prepared in LB-antibiotic liquid medium on a rotary shaker (250 rpm) at 37°, using procedures recommended in the pET System Manual to maximize pET plasmid retention. At an $OD_{525}$ of 2.4, cells from this 200 ml culture were collected by centrifugation and resuspended in 50 ml of fresh medium. This suspension was transferred to a high density fermentor containing 4 liters of carbenicillin- and chloramphenicol-containing SLBH medium (the composition of SLBH medium, and the design and operation of the fermentor are described in (Sadler et al. 1974)). After 20 hours of growth under $O_2$ at 32° ($OD_{525}$=19) isopropylthiogalactoside (IPTG) was added to 0.4 mM to induce uricase production. After 6 more hours ($OD_{525}$=37) bacterial cells were harvested by centrifugation (10,410×g, 10 min, 4° C.), washed once with PBS, and stored frozen at −20° C.

The bacterial cells (189 g) were resuspended in 200 ml PBS and lysed while cooled in an ice/salt bath by sonication (Heat Systems Sonicator XL, probe model CL, Farmingdale, N.Y.) for 4×40 second bursts at 100% intensity, with a 1 minute rest between bursts. PBS-insoluble material (which includes uricase) was pelleted by centrifugation (10,410×g, 10 min, 4° C.), and was then washed 5 times with 200 ml PBS. Uricase in the PBS-insoluble pellet was extracted into 80 ml of 1 M $Na_2CO_3$, pH 10.2 containing 1 mM phenylmethylsulfonylfluoride (PMSF) and 130 µg/ml aprotinin. Insoluble debris was removed by centrifugation (20,190×g, 2 hours, 4° C.). All further steps in purification were at 4° C. (results summarized in Table 3).

The pH 10.2 extract was diluted to 1800 ml with 1 mM PMSF (to reduce $Na_2CO_3$ to 0.075 M). This was applied to a column (2.6×9 cm) of fresh Q-Sepharose (Pharmacia Biotech, Inc., Piscataway, N.J.), which had been equilbrated with 0.075 M $Na_2CO_3$, pH 10.2. After loading, the column was washed successively with 1) 0.075 M $Na_2CO_3$, pH 10.2 until $A_{280}$ absorbance of the effluent reached background; 2) 10 mM $NaHCO_3$, pH 8.5 until the effluent pH fell to 8.5; 3) 50 ml of 10 mM $NaHCO_3$, pH 8.5, 0.15 M NaCl; 4) a 100-ml gradient of 0.15 M to 1.5 M NaCl in 10 mM $NaHCO_3$, pH 8.5; 5) 150 ml of 10 mM $NaHCO_3$ pH 8.5, 1.5 M NaCl; 6) 10 mM $NaHCO_3$ pH 8.5; 7) 0.1 M $Na_2CO_3$, pH 11 until the effluent pH was raised to 11. Finally, uricase was eluted with a 500 ml gradient from 0 to 0.6 M NaCl in 0.1 M $Na_2CO_3$, pH 11. The activity eluted in two $A_{280}$-absorbing peaks, which were pooled separately (Fraction A and Fraction B, Table 3). Uricase in each of these pools was then precipitated by lowering the pH to 7.1 by slow addition of 1 M acetic acid, followed by centrifugation (7,000×g, 10 min). The resulting pellets were dissolved in 50 ml of 1 M $Na_2CO_3$, pH 10.2 and stored at 4° C.

TABLE 3

Recombinant Pig-Baboon Chimeric (PBC) Uricase Purification
IPTG-induced Cell Paste = 189.6 g

| Fraction | Total Protein mg | Uricase activity U/ml | Total Uricase Units | Specific Activity U/mg |
|---|---|---|---|---|
| pH 7 Sonicate + pH 7 Wash | | | 74.9 | |
| pH 10.2 Extract | 4712 | 82.7 | 11,170 | 2.4 |
| Q-Sepharose | | | | |
| fraction A | 820 | 11.5 | 1,081* | 1.9 |
| fraction B | 1809 | 31.7 | 4,080 | 2.3 |
| pH 7.1 precipitated & redissolved | | | | |
| fraction A | 598 | 35.0 | 1,748 | 3.0 |
| fraction B | 1586 | 75.5 | 3,773 | 2.4 |
| Total Recovery | 2184 | | 5,521 | |

EXAMPLE 3

Small Scale Preparation and PEGylation of Recombinant PBC Uricase.

This example shows that purified recombinant PBC uricase can be used to produce a PEGylated uricase. In this reaction, all uricase subunits were modified (FIG. 1, lane 7), with retention of about 60% of catalytic activity (Table 4).

A. Small Scale Expression and Isolation of PBC Uricase (Table 4, FIG. 1).

A 4-liter culture of *E. coli* BL21(DE3)pLysS transformed with pET3d-PBC cDNA was incubated on a rotary shaker (250 rpm) at 37°. At 0.7 $OD_{525}$, the culture was induced with IPTG (0.4 mM, 6 hours). The cells were harvested and frozen at −20° C. The cells (15.3 g) were disrupted by freezing and thawing, and extracted with 1 M $Na_2CO_3$, pH 10.2, 1 mM PMSF. After centrifugation (12,000×g, 10 min, 4° C.) the supernatant (85 ml) was diluted 1:10 with water and then chromatographed on Q-Sepharose in a manner similar to that described in Example 1. Pooled uricase activity from this step was concentrated by pressure ultrafiltration using a PM30 membrane (Amicon, Beverly, Mass.). The concentrate was chromatographed on a column (2.5×100 cm) of Sephacryl S-200 (Pharmacia Biotech, Piscataway, N.J.) that was equilibrated and run in 0.1 M $Na_2CO_3$, pH 10.2. Fractions containing uricase activity were pooled and concentrated by pressure ultrafiltration, as above.

B. PEGylation.

100 mg of concentrated Sepahacryl S-200 PBC uricase (5 mg/ml, 2.9 µmol enzyme; 84.1 µmol lysine) in 0.1 M Na$_2$CO$_3$, pH 10.2 was allowed to react with a 2-fold excess (mol of PEG:mol uricase lysines) of an activated form of PEG at 4° for 60 min. The PEGylated uricase was freed from any unreacted or hydrolyzed PEG by tangential flow diafiltration. In this step the reaction was diluted 1:10 in 0.1 M Na$_2$CO$_3$, pH 10.2 and diafiltered vs. 3.5 vol 0.1 M Na$_2$CO$_3$, pH 10.2, then vs. 3.5 vol 0.05 M sodium phosphate, 0.15 M NaCl, pH 7.2. The filter-sterilized enzyme was stable at 4° for at least one month.

TABLE 4

Summary of Purification and PEGylation of Recombinant Pig-Baboon Chimeric (PBC) Uricase

| A. Purification Fraction | Total protein mg | Total uricase activity umol/min | Specific activity umol/min/mg | Recovery of activity % |
|---|---|---|---|---|
| Crude extract | 1565 | 1010 | 0.6 | 100 |
| Q-Sepharose | 355 | 1051 | 3.0 | 104 |
| Sephacryl S-200 | 215 | 1170 | 5.5 | 116 |
| B. PEGylation | | | | |
| S-200 uricase | 100 | 546 | 5.5 | 100 |
| PEG-uricase | 97 | 336 | 3.5 | 62 |

FIG. 1 shows a SDS-mercaptoethanol PAGE (12% gel) analysis of fractions obtained during the purification and PEGylation of recombinant pig baboon chimera (PBC) uricase. Lanes: 1=MW markers; 2=SDS extract of uninduced pET3d-PBC cDNA-transformed cells (*E. coli* BL21 (DE3)pLysS); 3=SDS extract of IPTG-induced pET-PBC cDNA-transformed cells; 4=Crude extract (see Table 5); 5=concentrated Q-sepharose uricase pool; 6=concentrated Sephacryl S-200 uricase pool; 7=PEGylated Sephacryl S-200 recombinant PBC uricase.

The results shown in Table 4 show that the purified PBC uricase could be modified with retention of about 60% of catalytic activity. In this PEGylation reaction all of the uricase subunits were modified (FIG. 1, lane 7). In studies not shown, the PEGylated enzyme had similar kinetic properties to unmodified PBC uricase ($K_M$ 10–20 μM). Importantly, the modified enzyme was much more soluble than the unmodified enzyme at physiologic pH (>5 mg/ml in PBS vs. <1 mg/ml). The PEGylated enzyme could also be lyophilized and then reconstituted in PBS, pH 7.2, with minimal loss of activity. In other experiments, we compared the activities of this preparation of PEG-PBC uricase with the *A. flavus* uricase clinical preparation. At pH 8.6 in borate buffer, the *A. flavus* enzyme had 10–14 fold higher Vmax and a 2 fold higher $K_M$. However, in PBS, pH 7.2, the PEG-PBC and unmodified fungal enzymes differed in uricase activity by <2 fold.

EXAMPLE 4

Circulating Life in Mice of Unmodified and PEGylated PBC Uricase.

Figure 2:
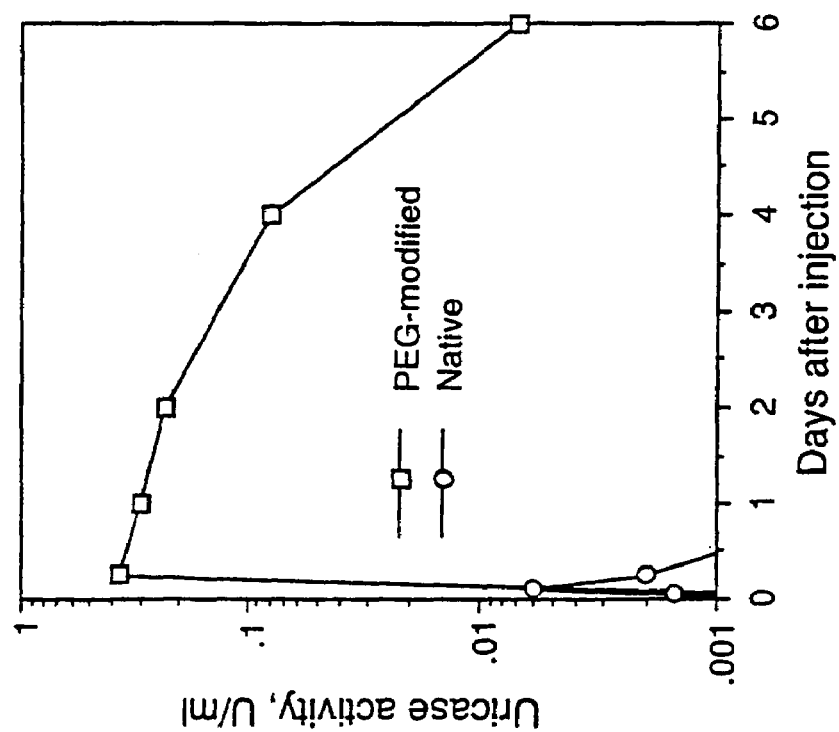
FIG. 2. Circulating life of native and PEGylated PBC uricase.

FIG. 2 shows the circulating life of native and PEGylated PBC uricase. Groups of mice (3 per time point) were injected IP with 1 unit of native (circles) or PEG-modified (squares) recombinant PBC uricase (preparation described in Example 3). At the indicated times, blood was obtained from sets of three mice for measuring serum uricase activity. The PEGylated uricase (described in Example 3) had a circulating half-life of about 48 hours, vs. <2 hours for the unmodified enzyme (FIG. 2).

EXAMPLE 5

Efficacy of PEGylated Uricase of Invention.

Figure 3:
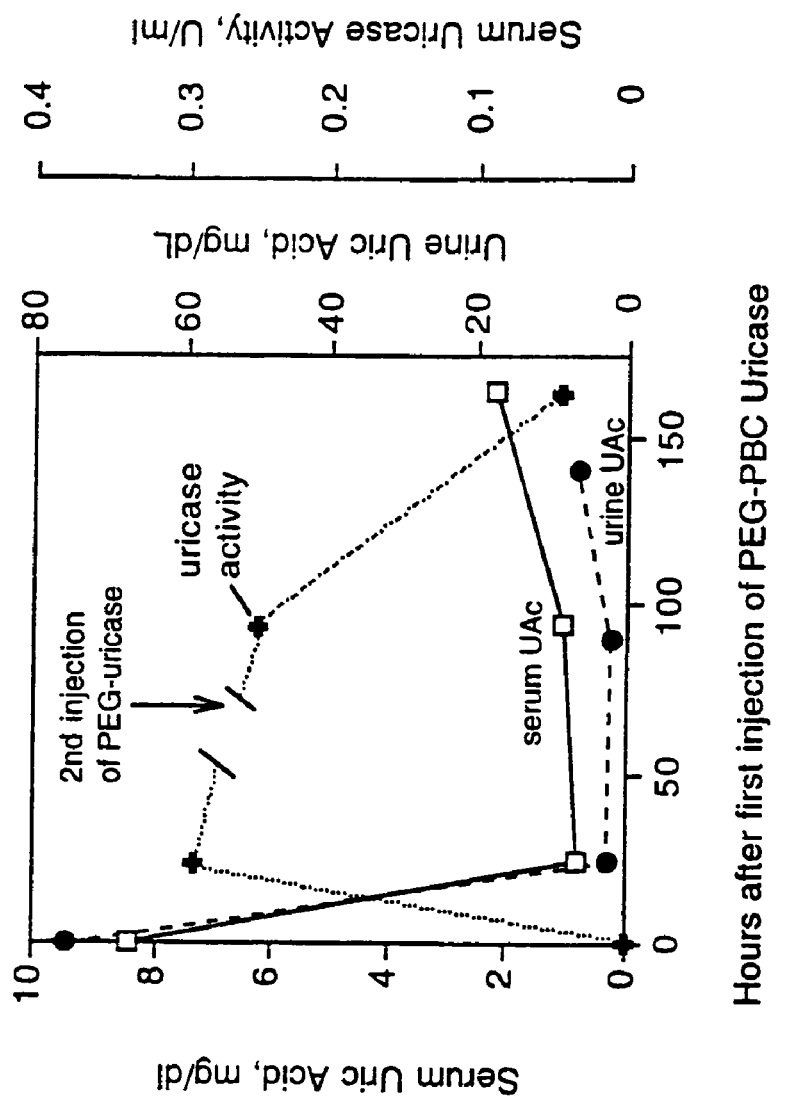
FIG. 3. Relationship of serum uricase activity to the serum and urine concentrations of uric acid.

FIG. 3 shows the relationship of serum uricase activity to the serum and urine concentrations of uric acid. In this experiment, a homozygous uricase-deficient knockout mouse (Wu et al. 1994) received two injections, at 0 and 72 hours, of 0.4 IU of recombinant PBC uricase that had been PEGylated. The uricase deficient knock-out mouse was used in this experiment because, unlike normal mice that have uricase, these knock-out mice, like humans, have high levels of uric acid in their blood and body fluids and excrete high levels of uric acid in their urine. These high levels of uric acid cause serious injury to the kidneys of these mice, which is often fatal (Wu et al. 1994).

The experiment shown in FIG. 3 demonstrates that intraperitoneal injections of a PEGylated preparation of recombinant PBC uricase resulted in an increase in serum uricase activity, which was accompanied by marked decline in the serum and urinary concentrations of uric acid in a uricase-deficient mouse.

EXAMPLE 6

Nonimmunogenicity of Construct-Carrier Complex

Figure 4:
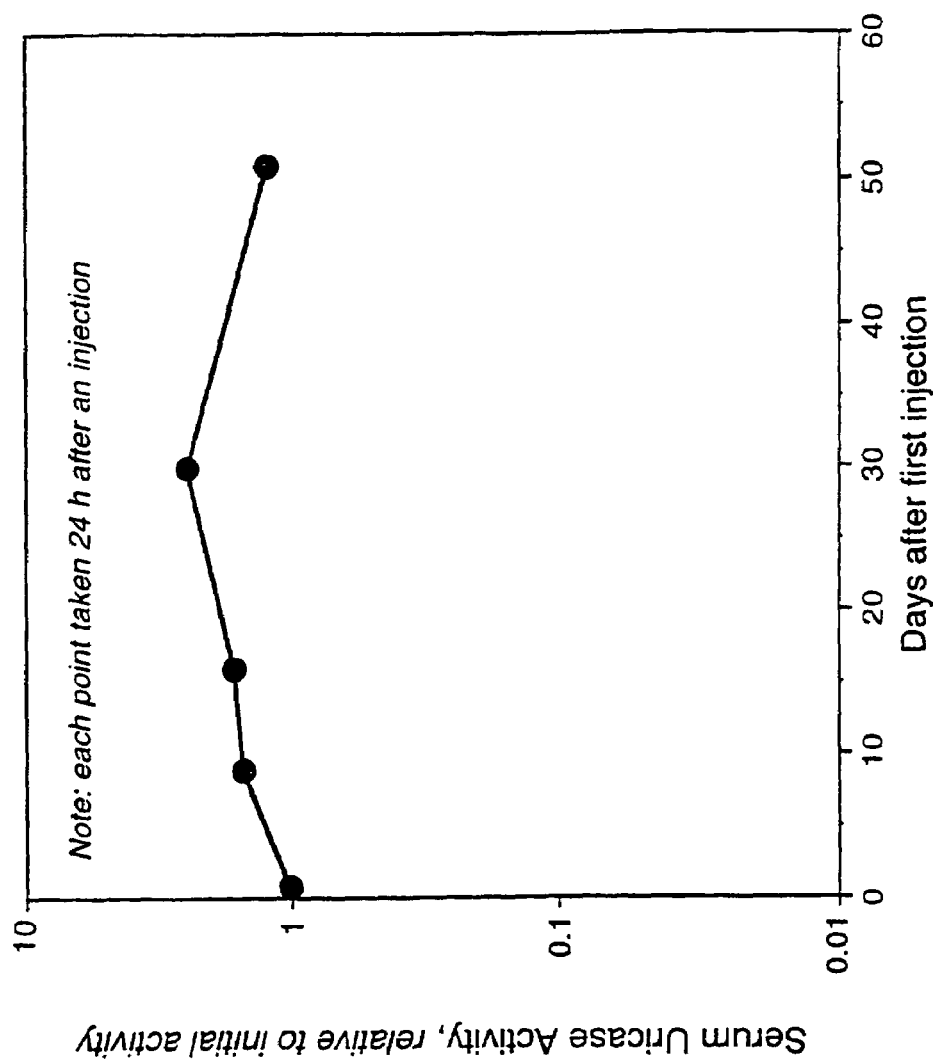
FIG. 4. Maintenance of circulating level of uricase activity (measured in serum) after repeated injection.

PEGylated recombinant PBC uricase was injected repeatedly into homozygous uricase-deficient mice without inducing accelerated clearance, consistent with absence of significant immunogenicity. This was confirmed by ELISA. FIG. 4 shows maintenance of circulating levels of uricase activity (measured in serum) after repeated injection. PEGylated PBC uricase was administered by intraperitoneal injection at 6–10 day intervals. Serum uricase activity was determined 24 hours post injection.

EXAMPLE 7

Covalent Linkage to Mutationally Introduced Lysine

PEGylation of purified recombinant PBC uricase should result in attachment of PEG to the novel lysine (residue 291). In this experiment a preparation of PBC uricase could be modified by PEGylation. It can be determined by means known in the art whether the peptide containing the novel lysine (residue 291) has been modified by PEGylation.

REFERENCES

Abuchowski A, Kazo G M, Verhoest C R, Jr., van Es T, Kafkewitz D, Nucci M L, Viau A T et al (1984) Cancer therapy with modified enzymes. I. Antitumor properties of polyethylene glycol-asparaginase conjugates. Cancer Biochem Biophys 7:175–186

Abuchowski A, McCoy J R, Palczuk N C, van Es T, Davis F F (1977a) Effect of attachment of polyethylene glycol on immunogenicity and circulating life of bovine liver catalase. J Biol Chem 252:3582–3586

Abuchowski A, van Es T, Palczuk N C, Davis F F (1977b) Alteration of immunological properties of bovine serum albumin by covalent attachment of polyethylene glycol. J Biol Chem 252:3578–3581

Ausubel F M (1998) Current Protocols in Molecular Biology John Wiley & Sons

Ahn K J, Kim Y S, Lee H C, Park K, Huh K B (1992) Cyclosporine-induced hyperuricemia after renal transplant: Clinical characteristics and mechanisms. Transplantation Proceedings 24:1391–1392

Arellano F, Sacristan J A (1993) Allopurinol hypersensitivity syndrome: A review. Ann Pharmacother 27:337–343

Becker M A (1988) Clinical aspects of monosodium urate monohydrate crystal deposition disease (gout). Rheumatic Disease Clinics of North America 14:377–394

Becker M A, Roessler B J (1995) Hyperuricemia and gout. In: Scriver C R, Beaudet A L, Sly W S, Valle D (eds) The Metabolic and Molecular Bases of Inherited Disease, 7 th ed. McGraw-Hill, New York, pp 1655–1677

Brogard J M, Coumaros D, Frankhauser J, Stahl A, Stahl J (1972) Enzymatic uricolysis: A study of the effect of a fungal urate-oxydase. Eur J Clin Biol Res 17:890–895

Brogard J M, Stahl A, Stahl J (1978) Enzymatic uricolysis and its use in therapy. In: Kelley W N, Arnold W J, Weiner I M (eds) Uric Acid, Springer-Verlag, New York, pp515–524

Chaffee S, Mary A, Stiehm E R, Girault D, Fischer A, Hershfield M S (1992) IgG antibody response to polyethylene glycol-modified adenosine deaminase (PEG-ADA) in patients with adenosine deaminase deficiency. J Clin Invest 89:1643–1651

Chen R H L, Abuchowski A, van Es T, Palczuk N C, Davis F F (1981) Properties of two urate oxidases modified by the covalent attachment of poly(ethylene glycol). Biochim Biophys Acta 660:293–298

Chua C C, Greenberg M L, Viau A T, Nucci M, Brenckman W D, Jr., Hershfield M S (1988) Use of polyethylene glycol-modified uricase (PEG-uricase) to treat hyperuricemia in a patient with non-Hodgkin lymphoma. Ann Int Med 109:114–117

Cohen L F, Balow J E, Magrath I T, Poplack D G, Ziegler J L (1980) Acute tumor lysis syndrome: A review of 37 patients with Burkitt's lymphoma. Am J Med 64:468–491

Conley T G, Priest D G (1979) Purification of uricase from mammalian tissue. Preparative Biochemistry 9:197–203

Davis F F, Kazo G M, Nucci M L, Abuchowski A (1991) Reduction of immunogenicity and extension of circulating life of peptides and proteins. In: Lee VHL (eds) Peptide and Protein Drug Delivery, Marcel Dekker, New York, pp831–864

Davis S, Abuchowski A, Park Y K, Davis F F (1981a) Alteration of the circulating life and antigenic properties of bovine adenosine deaminase in mice by attachment of polyethylene glycol. Clin Exp Immunol 46:649–652

Davis S, Park Y K, Abuchowski A, Davis F F (1981b) Hypouricaemic effect of polyethylene glycol modified urate oxidase. Lancet 1:281–283

Delaney V, Sumrani N, Daskalakis P, Hong J H, Sommer B G (1992) Hyperuricemia and gout in renal allograft recipients. Transplantation Proceedings 24:1773–1774

Donadio D, Errera J, Navarro M, Izarn P (1981) Anaphylaxis-like manifestations after intravenous injection of urate oxidase in an asthmatic child with acute leukemia (letter). Nouv Presse Med 10:711–712

Erlich H A (1989) PCR Technology. Principles and applications for DNA amplification Stockton Press, New York Escudier B, Leclercq B, Tandonnet F, Nitenberg G (1984) Hyperuricemia resistant to urate oxidase. Efficacy of high doses (letter). Presse Med 13:1340

Fam A G (1990) Strategies and controversies in the treatment of gout and hyperuricaemia. Balliere's Clinical Rheumatology 4:177–192

George T, Mandell B F (1995) Gout in the transplant patient. J Clin Rheumatol 1:328–334

Gold G L, Fritz B D (1957) Hyperuricemia associated with the treatment of leukemia. Ann Int Med 47:428–434

Greenberg M L, Hershfield M S (1989) A radiochemical-high-performance liquid chromatographic assay for urate oxidase in human plasma. Anal Biochem 176:290–293

Harris J M, Zalipsky S (Ed.) (1997) Poly(ethylene glycol) Chemistry and Biological ApplicationsACS, Washington, D.C.

Hershfield M, S. (1997) Biochemistry and immunology of poly(ethylene glycol)-modified adenosine deaminase (PEG-ADA). In: Harris J M, Zalipsky S (eds) Poly (ethylene glycol) Chemistry and Biological Applications, ACS, Washington, D.C., pp145–154

Hershfield M S (1995) PEG-ADA replacement therapy for adenosine deaminase deficiency: An update after 8.5 years. Clin Immunol Immunopathol 76:S228–S232

Hershfield M S (1996) Gout and uric acid metabolism. In: Bennett J C, Plum F (eds) Cecil Textbook of Medicine, XX ed. W B Saunders, New York, pp1508–1515

Hershfield M S, Buckley R H, Greenberg M L, Melton A L, Schiff R, Hatem C, Kurtzberg J et al (1987) Treatment of adenosine deaminase deficiency with polyethylene glycol-modified adenosine deaminase. N Engl J Med 316: 589–596

Hershfield M S, Chaffee S, Koro-Johnson L, Mary A, Smith A A, Short S A (1991) Use of site-directed mutagenesis to enhance the epitope shielding effect of covalent modification of proteins with polyethylene glycol. Proc Natl Acad Sci USA 88:7185–7189

Hershfield M S, Mitchell B S (1995) Immunodeficiency diseases caused by adenosine deaminase deficiency and purine nucleoside phosphorylase deficiency. In: Scriver C R, Beaudet A L, Sly W S, Valle D (eds) The Metabolic and Molecular Bases of Inherited Disease, 7 th ed. McGraw-Hill, New York, pp1725–1768

Hershfield M S, Seegmiller J E (1976) Gout and the regulation of purine biosynthesis. In: Quagliariello E (eds) Horizons in Biochemistry and Biophysics, Addison-Wesley, Reading, M A, pp134–162

Jones D P, Stapleton F B, Kalwinsky D, McKay C P, Kellie S J, Pui C H (1990) Renal dysfunction and hyperuricemia at presentation and relapse of acute lymphoblastic leukemia. Med Pediatr Oncol 18:283–286

Kelley W N, Fox I H, Pallela T D (1989) Gout and related disorders of purine metabolism. In: Kelley W N, Harris E D, Ruddy S, Sledge C G (eds) Textbook of Rheumatology, 3rd ed. W B Saunders, Philadelphia, pp1395–1448

Kissel P, Lamarche M, Royer R (1968) Modification of uricaemia and the excretion of uric acid nitrogen by an enzyme of fungal origin. Nature 217:72–74

Kissel P, Schmitt J, Streiff F, Makuary G, Schmidt C, Toussain P (1972) L'urate oxydase: son intérêt dans la prévention des hyperuricemies therapeutiques en hematologie. Ann Med Nancy 11:519–535

Lee C C, Wu X, Gibbs R A, Cook R G, Muzny D M, Caskey C T (1988) Generation of cDNA directed by amino acid sequence: Cloning of urate oxidase. Science 239:1288–1291

Legoux R, Delpech B, Dumont X, Guillemot J C, Ramond P, Shire D, Caput D et al (1992) Cloning and expression in *Escherichia coli* of the gene encoding *Aspergillus flavus* urate oxidase. J Biol Chem 267:8565–8570

London M. Hudson P M (1957) Uricolytic activity of purified uricase in two human beings. Science 125:937–938

Masera G, Jankovic M, Zurlo M G, Locasciulli A, Rossi M R, Uderzo C, Recchia M (1982) Urate-oxidase prophylaxis of uric acid-induced renal damage in childhood leukemia. J Pediatr 100:152–155

Montagnac R, Schillinger F (1990) Anaphylactic complication tied to intravenous injection of urate oxidase. Nephrologie 11:259

Mourad G, Cristol J P, Chong G, Andary M, Mion C (1984) Role of precipitating anti-urate oxidase antibodies in urate oxidase-resistant hyperuricemia (letter). Presse Med 13:2585

Potaux L, Aparicio M, Maurel C, Ruedas M E, Martin-Dupont C L (1975) Uricolytic therapy. Value of urate oxidase in the treatment of hyperuricemiasi. Nouv Presse Med 4:1109–1112

Priest D G, Pitts O M (1972) Reaction intermediate effects on the spectrophotometric uricase assay. Analytical Biochemistry 50:195–205

Pui C-H, Relling M V, Lascombes F, Harrison P L, Struxiano A, Mondesir J-M, Riberio R C et al (1997) Urate oxidase in prevention and treatment of hyperuricemia associated with lymphoid malignancies. Leukemia 11:1813–1816

Reddy P G, Nemali M R, Reddy M K, Reddy M N, Yuan P M, Yuen S, Laffler T G et al (1988) Isolation and sequence determination of a cDNA clone for rat peroxisomal urate oxidase: Liver-specific expression in the rat. Proc Natl Acad Sci USA 85:9081–9085

Rosenthal A K, Ryan L M (1995) Treatment of refractory crystal-associated arthtitis. Rheum Dis Clin North Amer 21:151–161

Roubenoff R (1990) Gout and hyperuricemia. Rheumatic Disease Clinics of North America 16:539–550

Sadler J R, Miwa J, Maas P, Smith T (1974) growth of high density bacterial cultures; a simple device. Laboratory Practice 23:632–643

Sambrook J, Fritsch E F, Maniatis T (1989) Molecular cloning. A laboratory manual 2 nd ed. Cold Spring Harbor Laboratory Press, Cold Spring Harbor, N.Y., Pages Sandberg A A, Cartwright G B, Wintrobe M M (1956) Studies on leukemia. I. Uric acid excretion. Blood 11:154–166

Savoca K V, Davis F F, Palczuk N C (1984) Induction of tolerance in mice by uricase and monomethoxypolyethylene glycol-modified uricase. Int Arch Allergy Appl Immunol 75:58–67

Sibony G, North M L, Bergerat W P, Lang J M, Oberling F (1984) Hyperuricemia resistant to urate oxidase. Role of anti-serum urate oxidase precipitating antibodies (letter). Presse Med 13:443

Singer J Z, Wallace S L (1986) The allopurinol hypersensitivity syndrome. Unnecessary morbidity and mortality. Arthritis Rheum 29:82–87

Tsuji J, Hirose K, Kasahara E, Naitoh M, Yamamoto I (1985) Studies on the antigenicity of the polyethylene glycol-modified uricase. Int J Immunopharmacol 7:725–730

Venkataseshan V S, Feingold R. Dikman S, Churg J (1990) Acute hyperuricemic nephropathy and renal failure after transplantation. Nephron 56:317–321

Veronese F M, Caliceti P, Schiavon O (1997) New synthetic polymers for enzyme and liposome modification. In: Harris J M, Zalipsky S (eds) Poly(ethylene glycol) Chemistry and Biological Applications, ACS, Washington, D.C., pp182–192

West C, Carpenter B J, Hakala T R (1987) The incidence of gout in renal transplant recipients. Am J Kidney Dis 10:369–371

Wu X, Lee C C, Muzny D M, Caskey C T (1989) Urate oxidase: Primary structure and evolutionary implications. Proc Natl Acad Sci USA 86:9412–9416

Wu X, Muzny D M, Lee C C, Caskey C T (1992) Two independent mutational events in the loss of urate oxidase. J Mol Evol 34:78–84

Wu X, Wakamiya M, Vaishnav S, Geske R, Montgomery C M, Jr., Jones P, Bradley A et al (1994) Hyperuricemia and urate nephropathy in urate oxidase-deficient mice. Proc Natl Acad Sci USA 91:742–746

Zittoun R, Dauchy F, Teillaud C, Barthelemy M, Bouchard P (1976) Le traitement des hyperuricemies en hematologie par l'urate-oxydase et l'allopurinol. Ann Med Interne 127:479–482

All documents cited above are incorporated herein, in their entirety, by reference.

We claim:

1. A protein comprising a recombinant uricase chimeric protein which comprises 304 amino acids, the first 225 N-terminal portion of said 304 amino acids being amino acids 1–225 of porcine uricase and the remaining 79 amino acids of said 304 amino acids being amino acids 226–304 of baboon uricase.

2. A protein comprising a recombinant uricase chimeric protein which comprises 304 amino acids, the first 288 N-terminal portion of said 304 amino acids being amino acids 1–288 of porcine uricase and the remaining 16 amino acids of said 304 amino acids being amino acids 289–304 of baboon uricase.

3. A recombinant uricase protein selected from the group consisting of SEQ ID NO:s 2, 4, 8, 9, 10 and 11.

4. An isolated and purified nucleic acid molecule coding for the recombinant uricase of claim 1.

5. An isolated and purified nucleic acid molecule coding for the recombinant uricase of claim 2.

6. An isolated and purified nucleic acid molecule coding for the recombinant uricase of claim 3.

7. An isolated and purified nucleic acid molecule of claim 6 having a base sequence of SEQ ID NO:1.

8. An isolated and purified nucleic acid molecule of claim 6 having a base sequence of SEQ ID NO:3.

9. A vector comprising a nucleic acid molecule of claim 6.

10. A host cell comprising a vector according to claim 9.

* * * * *

SEQUENCE LISTING

```
<160> NUMBER OF SEQ ID NOS: 13

<210> SEQ ID NO 1
<211> LENGTH: 915
<212> TYPE: DNA
<213> ORGANISM: Artificial Sequence
<220> FEATURE:
<221> NAME/KEY: CDS
<222> LOCATION: (1)..(915)
<220> FEATURE:
<223> OTHER INFORMATION: Description of Artificial Sequence:PBC CHIMERA

<400> SEQUENCE: 1 atg gct cat tac cgt aat gac tac aaa aag aat gat gag gta gag ttt        48
Met Ala His Tyr Arg Asn Asp Tyr Lys Lys Asn Asp Glu Val Glu Phe
 1               5                  10                  15 gtc cga act ggc tat ggg aag gat atg ata aaa gtt ctc cat att cag        96
Val Arg Thr Gly Tyr Gly Lys Asp Met Ile Lys Val Leu His Ile Gln
             20                  25                  30
```

```
cga gat gga aaa tat cac agc att aaa gag gtg gca act tca gtg caa       144
Arg Asp Gly Lys Tyr His Ser Ile Lys Glu Val Ala Thr Ser Val Gln
         35                  40                  45 ctg act ttg agc tcc aaa aaa gat tac ctg cat gga gac aat tca gat       192
Leu Thr Leu Ser Ser Lys Lys Asp Tyr Leu His Gly Asp Asn Ser Asp
 50                  55                  60 gtc atc cct aca gac acc atc aag aac aca gtt aat gtc ctg gcg aag       240
Val Ile Pro Thr Asp Thr Ile Lys Asn Thr Val Asn Val Leu Ala Lys
 65                  70                  75                  80 ttc aaa ggc atc aaa agc ata gaa act ttt gct gtg act atc tgt gag       288
Phe Lys Gly Ile Lys Ser Ile Glu Thr Phe Ala Val Thr Ile Cys Glu
                 85                  90                  95 cat ttc ctt tct tcc ttc aag cat gtc atc aga gct caa gtc tat gtg       336
His Phe Leu Ser Ser Phe Lys His Val Ile Arg Ala Gln Val Tyr Val
             100                 105                 110 gaa gaa gtt cct tgg aag cgt ttt gaa aag aat gga gtt aag cat gtc       384
Glu Glu Val Pro Trp Lys Arg Phe Glu Lys Asn Gly Val Lys His Val
             115                 120                 125 cat gca ttt att tat act cct act gga acg cac ttc tgt gag gtt gaa       432
His Ala Phe Ile Tyr Thr Pro Thr Gly Thr His Phe Cys Glu Val Glu
130                 135                 140 cag ata agg aat gga cct cca gtc att cat tct gga atc aaa gac cta       480
Gln Ile Arg Asn Gly Pro Pro Val Ile His Ser Gly Ile Lys Asp Leu
145                 150                 155                 160 aaa gtc ttg aaa aca acc cag tct ggc ttt gaa gga ttc atc aag gac       528
Lys Val Leu Lys Thr Thr Gln Ser Gly Phe Glu Gly Phe Ile Lys Asp
                 165                 170                 175 cag ttc acc acc ctc cct gag gtg aag gac cgg tgc ttt gcc acc caa       576
Gln Phe Thr Thr Leu Pro Glu Val Lys Asp Arg Cys Phe Ala Thr Gln
             180                 185                 190 gtg tac tgc aaa tgg cgc tac cac cag ggc aga gat gtg gac ttt gag       624
Val Tyr Cys Lys Trp Arg Tyr His Gln Gly Arg Asp Val Asp Phe Glu
             195                 200                 205 gcc acc tgg gac act gtt agg agc att gtc ctg cag aaa ttt gct ggg       672
Ala Thr Trp Asp Thr Val Arg Ser Ile Val Leu Gln Lys Phe Ala Gly
210                 215                 220 ccc tat gac aaa ggc gag tac tca ccc tct gtg cag aag acc ctc tat       720
Pro Tyr Asp Lys Gly Glu Tyr Ser Pro Ser Val Gln Lys Thr Leu Tyr
225                 230                 235                 240 gat atc cag gtg ctc tcc ctg agc cga gtt cct gag ata gaa gat atg       768
Asp Ile Gln Val Leu Ser Leu Ser Arg Val Pro Glu Ile Glu Asp Met
                 245                 250                 255 gaa atc agc ctg cca aac att cac tac ttc aat ata gac atg tcc aaa       816
Glu Ile Ser Leu Pro Asn Ile His Tyr Phe Asn Ile Asp Met Ser Lys
             260                 265                 270 atg ggt ctg atc aac aag gaa gag gtc ttg ctg cca tta gac aat cca       864
Met Gly Leu Ile Asn Lys Glu Glu Val Leu Leu Pro Leu Asp Asn Pro
             275                 280                 285 tat gga aaa att act ggt aca gtc aag agg aag ttg tct tca aga ctg       912
Tyr Gly Lys Ile Thr Gly Thr Val Lys Arg Lys Leu Ser Ser Arg Leu
290                 295                 300 tga                                                                   915

<210> SEQ ID NO 2
<211> LENGTH: 304
<212> TYPE: PRT
<213> ORGANISM: Artificial Sequence
<220> FEATURE:
<223> OTHER INFORMATION: Description of Artificial Sequence:PBC CHIMERA
```

<400> SEQUENCE: 2

```
Met Ala His Tyr Arg Asn Asp Tyr Lys Lys Asn Asp Glu Val Glu Phe
1               5                   10                  15

Val Arg Thr Gly Tyr Gly Lys Asp Met Ile Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Val Ile Pro Thr Asp Thr Ile Lys Asn Thr Val Asn Val Leu Ala Lys
65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
    130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300
```

<210> SEQ ID NO 3
<211> LENGTH: 915
<212> TYPE: DNA
<213> ORGANISM: Artificial Sequence
<220> FEATURE:
<221> NAME/KEY: CDS
<222> LOCATION: (1)..(915)
<220> FEATURE:
<223> OTHER INFORMATION: Description of Artificial Sequence:pks chimera

<400> SEQUENCE: 3

```
atg gct cat tac cgt aat gac tac aaa aag aat gat gag gta gag ttt    48
Met Ala His Tyr Arg Asn Asp Tyr Lys Lys Asn Asp Glu Val Glu Phe
1               5                   10                  15 gtc cga act ggc tat ggg aag gat atg ata aaa gtt ctc cat att cag    96
Val Arg Thr Gly Tyr Gly Lys Asp Met Ile Lys Val Leu His Ile Gln
            20                  25                  30
```

```
cga gat gga aaa tat cac agc att aaa gag gtg gca act tca gtg caa    144
Arg Asp Gly Lys Tyr His Ser Ile Lys Glu Val Ala Thr Ser Val Gln
         35                  40                  45 ctg act ttg agc tcc aaa aaa gat tac ctg cat gga gac aat tca gat    192
Leu Thr Leu Ser Ser Lys Lys Asp Tyr Leu His Gly Asp Asn Ser Asp
 50                  55                  60 gtc atc cct aca gac acc atc aag aac aca gtt aat gtc ctg gcg aag    240
Val Ile Pro Thr Asp Thr Ile Lys Asn Thr Val Asn Val Leu Ala Lys
 65                  70                  75                  80 ttc aaa ggc atc aaa agc ata gaa act ttt gct gtg act atc tgt gag    288
Phe Lys Gly Ile Lys Ser Ile Glu Thr Phe Ala Val Thr Ile Cys Glu
                 85                  90                  95 cat ttc ctt tct tcc ttc aag cat gtc atc aga gct caa gtc tat gtg    336
His Phe Leu Ser Ser Phe Lys His Val Ile Arg Ala Gln Val Tyr Val
             100                 105                 110 gaa gaa gtt cct tgg aag cgt ttt gaa aag aat gga gtt aag cat gtc    384
Glu Glu Val Pro Trp Lys Arg Phe Glu Lys Asn Gly Val Lys His Val
         115                 120                 125 cat gca ttt att tat act cct act gga acg cac ttc tgt gag gtt gaa    432
His Ala Phe Ile Tyr Thr Pro Thr Gly Thr His Phe Cys Glu Val Glu
130                 135                 140 cag ata agg aat gga cct cca gtc att cat tct gga atc aaa gac cta    480
Gln Ile Arg Asn Gly Pro Pro Val Ile His Ser Gly Ile Lys Asp Leu
145                 150                 155                 160 aaa gtc ttg aaa aca acc cag tct ggc ttt gaa gga ttc atc aag gac    528
Lys Val Leu Lys Thr Thr Gln Ser Gly Phe Glu Gly Phe Ile Lys Asp
                 165                 170                 175 cag ttc acc acc ctc cct gag gtg aag gac cgg tgc ttt gcc acc caa    576
Gln Phe Thr Thr Leu Pro Glu Val Lys Asp Arg Cys Phe Ala Thr Gln
             180                 185                 190 gtg tac tgc aaa tgg cgc tac cac cag ggc aga gat gtg gac ttt gag    624
Val Tyr Cys Lys Trp Arg Tyr His Gln Gly Arg Asp Val Asp Phe Glu
         195                 200                 205 gcc acc tgg gac act gtt agg agc att gtc ctg cag aaa ttt gct ggg    672
Ala Thr Trp Asp Thr Val Arg Ser Ile Val Leu Gln Lys Phe Ala Gly
210                 215                 220 ccc tat gac aaa ggc gag tac tcg ccc tct gtc cag aag aca ctc tat    720
Pro Tyr Asp Lys Gly Glu Tyr Ser Pro Ser Val Gln Lys Thr Leu Tyr
225                 230                 235                 240 gac atc cag gtg ctc acc ctg ggc cag gtt cct gag ata gaa gat atg    768
Asp Ile Gln Val Leu Thr Leu Gly Gln Val Pro Glu Ile Glu Asp Met
                 245                 250                 255 gaa atc agc ctg cca aat att cac tac tta aac ata gac atg tcc aaa    816
Glu Ile Ser Leu Pro Asn Ile His Tyr Leu Asn Ile Asp Met Ser Lys
             260                 265                 270 atg gga ctg atc aac aag gaa gag gtc ttg cta cct tta gac aat cca    864
Met Gly Leu Ile Asn Lys Glu Glu Val Leu Leu Pro Leu Asp Asn Pro
         275                 280                 285 tat gga aaa att act ggt aca gtc aag agg aag ttg tct tca aga ctg    912
Tyr Gly Lys Ile Thr Gly Thr Val Lys Arg Lys Leu Ser Ser Arg Leu
290                 295                 300 tga                                                                915

<210> SEQ ID NO 4
<211> LENGTH: 304
<212> TYPE: PRT
<213> ORGANISM: Artificial Sequence
<220> FEATURE:
<223> OTHER INFORMATION: Description of Artificial Sequence:pks chimera
```

<400> SEQUENCE: 4

```
Met Ala His Tyr Arg Asn Asp Tyr Lys Lys Asn Asp Glu Val Glu Phe
  1               5                  10                  15

Val Arg Thr Gly Tyr Gly Lys Asp Met Ile Lys Val Leu His Ile Gln
             20                  25                  30

Arg Asp Gly Lys Tyr His Ser Ile Lys Glu Val Ala Thr Ser Val Gln
         35                  40                  45

Leu Thr Leu Ser Ser Lys Lys Asp Tyr Leu His Gly Asp Asn Ser Asp
     50                  55                  60

Val Ile Pro Thr Asp Thr Ile Lys Asn Thr Val Asn Val Leu Ala Lys
 65                  70                  75                  80

Phe Lys Gly Ile Lys Ser Ile Glu Thr Phe Ala Val Thr Ile Cys Glu
                 85                  90                  95

His Phe Leu Ser Ser Phe Lys His Val Ile Arg Ala Gln Val Tyr Val
                100                 105                 110

Glu Glu Val Pro Trp Lys Arg Phe Glu Lys Asn Gly Val Lys His Val
            115                 120                 125

His Ala Phe Ile Tyr Thr Pro Thr Gly Thr His Phe Cys Glu Val Glu
        130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
                245                 250                 255

Glu Ile Ser Leu Pro Asn Ile His Tyr Leu Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300
```

<210> SEQ ID NO 5
<211> LENGTH: 304
<212> TYPE: PRT
<213> ORGANISM: Artificial Sequence
<220> FEATURE:
<223> OTHER INFORMATION: Description of Artificial Sequence:baboon D3H

<400> SEQUENCE: 5

```
Met Ala His Tyr His Asn Asn Tyr Lys Lys Asn Asp Glu Leu Glu Phe
  1               5                  10                  15

Val Arg Thr Gly Tyr Gly Lys Asp Met Val Lys Val Leu His Ile Gln
             20                  25                  30

Arg Asp Gly Lys Tyr His Ser Ile Lys Glu Val Ala Thr Ser Val Gln
         35                  40                  45

Leu Thr Leu Ser Ser Lys Lys Asp Tyr Leu His Gly Asp Asn Ser Asp
```

```
                 50                  55                  60
Ile Ile Pro Thr Asp Thr Ile Lys Asn Thr Val His Val Leu Ala Lys
 65                  70                  75                  80

Phe Lys Gly Ile Lys Ser Ile Glu Ala Phe Gly Val Asn Ile Cys Glu
                 85                  90                  95

Tyr Phe Leu Ser Ser Phe Asn His Val Ile Arg Ala Gln Val Tyr Val
                100                 105                 110

Glu Glu Ile Pro Trp Lys Arg Leu Glu Lys Asn Gly Val Lys His Val
            115                 120                 125

His Ala Phe Ile His Thr Pro Thr Gly Thr His Phe Cys Glu Val Glu
130                 135                 140

Gln Leu Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
                180                 185                 190

Val Tyr Cys Lys Trp Arg Tyr His Gln Cys Arg Asp Val Asp Phe Glu
            195                 200                 205

Ala Thr Trp Gly Thr Ile Arg Asp Leu Val Leu Glu Lys Phe Ala Gly
210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
        290                 295                 300

<210> SEQ ID NO 6
<211> LENGTH: 304
<212> TYPE: PRT
<213> ORGANISM: baboon

<400> SEQUENCE: 6

Met Ala Asp Tyr His Asn Asn Tyr Lys Lys Asn Asp Glu Leu Glu Phe
 1               5                  10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Asp Tyr Leu His Gly Asp Asn Ser Asp
    50                  55                  60

Ile Ile Pro Thr Asp Thr Ile Lys Asn Thr Val His Val Leu Ala Lys
 65                  70                  75                  80

Phe Lys Gly Ile Lys Ser Ile Glu Ala Phe Gly Val Asn Ile Cys Glu
                85                  90                  95

Tyr Phe Leu Ser Ser Phe Asn His Val Ile Arg Ala Gln Val Tyr Val
                100                 105                 110

Glu Glu Ile Pro Trp Lys Arg Leu Glu Lys Asn Gly Val Lys His Val
            115                 120                 125
```

```
His Ala Phe Ile His Thr Pro Thr Gly Thr His Phe Cys Glu Val Glu
        130                 135                 140

Gln Leu Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Cys Arg Asp Val Asp Phe Glu
        195                 200                 205

Ala Thr Trp Gly Thr Ile Arg Asp Leu Val Leu Glu Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Val Leu Leu Pro Leu Asp Asn Pro
        275                 280                 285

Tyr Gly Lys Ile Thr Gly Thr Val Lys Arg Lys Leu Ser Ser Arg Leu
290                 295                 300
```

<210> SEQ ID NO 7
<211> LENGTH: 304
<212> TYPE: PRT
<213> ORGANISM: pig

<400> SEQUENCE: 7

```
Met Ala His Tyr Arg Asn Asp Tyr Lys Lys Asn Asp Glu Val Glu Phe
  1               5                  10                  15

Val Arg Thr Gly Tyr Gly Lys Asp Met Ile Lys Val Leu His Ile Gln
                20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Leu His Gly Asp Asn Ser Asp
    50                  55                  60

Val Ile Pro Thr Asp Thr Ile Lys Asn Thr Val Asn Val Leu Ala Lys
65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
    130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205
```

```
Ala Thr Trp Asp Thr Val Arg Ser Ile Val Leu Gln Lys Phe Ala Gly
        210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
                245                 250                 255

Glu Ile Ser Leu Pro Asn Ile His Tyr Leu Asn Ile Asp Met Ser Lys
                260                 265                 270

Met Gly Leu Ile Asn Lys Glu Glu Val Leu Leu Pro Leu Asp Asn Pro
        275                 280                 285

Tyr Gly Arg Ile Thr Gly Thr Val Lys Arg Lys Leu Thr Ser Arg Leu
        290                 295                 300

<210> SEQ ID NO 8
<211> LENGTH: 298
<212> TYPE: PRT
<213> ORGANISM: Artificial Sequence
<220> FEATURE:
<223> OTHER INFORMATION: Description of Artificial Sequence:PBC amino
      truncated

<400> SEQUENCE: 8

Asp Tyr Lys Lys Asn Asp Glu Val Glu Phe Val Arg Thr Gly Tyr Gly
1               5                   10                  15

Lys Asp Met Ile Lys Val Leu His Ile Gln Arg Asp Gly Lys Tyr His
                20                  25                  30

Ser Ile Lys Glu Val Ala Thr Ser Val Gln Leu Thr Leu Ser Ser Lys
            35                  40                  45

Lys Asp Tyr Leu His Gly Asp Asn Ser Asp Val Ile Pro Thr Asp Thr
        50                  55                  60

Ile Lys Asn Thr Val Asn Val Leu Ala Lys Phe Lys Gly Ile Lys Ser
65                  70                  75                  80

Ile Glu Thr Phe Ala Val Thr Ile Cys Glu His Phe Leu Ser Ser Phe
                85                  90                  95

Lys His Val Ile Arg Ala Gln Val Tyr Val Glu Glu Val Pro Trp Lys
                100                 105                 110

Arg Phe Glu Lys Asn Gly Val Lys His Val His Ala Phe Ile Tyr Thr
            115                 120                 125

Pro Thr Gly Thr His Phe Cys Glu Val Glu Gln Ile Arg Asn Gly Pro
        130                 135                 140

Pro Val Ile His Ser Gly Ile Lys Asp Leu Lys Val Leu Lys Thr Thr
145                 150                 155                 160

Gln Ser Gly Phe Glu Gly Phe Ile Lys Asp Gln Phe Thr Thr Leu Pro
                165                 170                 175

Glu Val Lys Asp Arg Cys Phe Ala Thr Gln Val Tyr Cys Lys Trp Arg
                180                 185                 190

Tyr His Gln Gly Arg Asp Val Asp Phe Glu Ala Thr Trp Asp Thr Val
            195                 200                 205

Arg Ser Ile Val Leu Gln Lys Phe Ala Gly Pro Tyr Asp Lys Gly Glu
        210                 215                 220

Tyr Ser Pro Ser Val Gln Lys Thr Leu Tyr Asp Ile Gln Val Leu Ser
225                 230                 235                 240

Leu Ser Arg Val Pro Glu Ile Glu Asp Met Glu Ile Ser Leu Pro Asn
                245                 250                 255

Ile His Tyr Phe Asn Ile Asp Met Ser Lys Met Gly Leu Ile Asn Lys
```

```
                260                 265                 270
Glu Glu Val Leu Leu Pro Leu Asp Asn Pro Tyr Gly Lys Ile Thr Gly
            275                 280                 285

Thr Val Lys Arg Lys Leu Ser Ser Arg Leu
            290                 295

<210> SEQ ID NO 9
<211> LENGTH: 301
<212> TYPE: PRT
<213> ORGANISM: Artificial Sequence
<220> FEATURE:
<223> OTHER INFORMATION: Description of Artificial Sequence:PBC carboxy
      truncated

<400> SEQUENCE: 9

Met Ala His Tyr Arg Asn Asp Tyr Lys Lys Asn Asp Glu Val Glu Phe
 1               5                  10                  15

Val Arg Thr Gly Tyr Gly Lys Asp Met Ile Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
 50                  55                  60

Val Ile Pro Thr Asp Thr Ile Lys Asn Thr Val Asn Val Leu Ala Lys
 65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
    130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser
    290                 295                 300

<210> SEQ ID NO 10
<211> LENGTH: 298
```

```
<212> TYPE: PRT
<213> ORGANISM: Artificial Sequence
<220> FEATURE:
<223> OTHER INFORMATION: Description of Artificial Sequence:PKS amino
      truncated

<400> SEQUENCE: 10
```

| | | | | | | | | | | | | | | | |
|---|---|---|---|---|---|---|---|---|---|---|---|---|---|---|---|
| Asp | Tyr | Lys | Lys | Asn | Asp | Glu | Val | Glu | Phe | Val | Arg | Thr | Gly | Tyr | Gly |
| 1 | | | | 5 | | | | | 10 | | | | | 15 | |
| Lys | Asp | Met | Ile | Lys | Val | Leu | His | Ile | Gln | Arg | Asp | Gly | Lys | Tyr | His |
| | | | 20 | | | | | 25 | | | | | 30 | | |
| Ser | Ile | Lys | Glu | Val | Ala | Thr | Ser | Val | Gln | Leu | Thr | Leu | Ser | Ser | Lys |
| | | 35 | | | | | 40 | | | | | 45 | | | |
| Lys | Asp | Tyr | Leu | His | Gly | Asp | Asn | Ser | Asp | Val | Ile | Pro | Thr | Asp | Thr |
| | 50 | | | | | 55 | | | | | 60 | | | | |
| Ile | Lys | Asn | Thr | Val | Asn | Val | Leu | Ala | Lys | Phe | Lys | Gly | Ile | Lys | Ser |
| 65 | | | | | 70 | | | | | 75 | | | | | 80 |
| Ile | Glu | Thr | Phe | Ala | Val | Thr | Ile | Cys | Glu | His | Phe | Leu | Ser | Ser | Phe |
| | | | | 85 | | | | | 90 | | | | | 95 | |
| Lys | His | Val | Ile | Arg | Ala | Gln | Val | Tyr | Val | Glu | Glu | Val | Pro | Trp | Lys |
| | | | 100 | | | | | 105 | | | | | 110 | | |
| Arg | Phe | Glu | Lys | Asn | Gly | Val | Lys | His | Val | His | Ala | Phe | Ile | Tyr | Thr |
| | | 115 | | | | | 120 | | | | | 125 | | | |
| Pro | Thr | Gly | Thr | His | Phe | Cys | Glu | Val | Glu | Gln | Ile | Arg | Asn | Gly | Pro |
| | 130 | | | | | 135 | | | | | 140 | | | | |
| Pro | Val | Ile | His | Ser | Gly | Ile | Lys | Asp | Leu | Lys | Val | Leu | Lys | Thr | Thr |
| 145 | | | | | 150 | | | | | 155 | | | | | 160 |
| Gln | Ser | Gly | Phe | Glu | Gly | Phe | Ile | Lys | Asp | Gln | Phe | Thr | Thr | Leu | Pro |
| | | | | 165 | | | | | 170 | | | | | 175 | |
| Glu | Val | Lys | Asp | Arg | Cys | Phe | Ala | Thr | Gln | Val | Tyr | Cys | Lys | Trp | Arg |
| | | | 180 | | | | | 185 | | | | | 190 | | |
| Tyr | His | Gln | Gly | Arg | Asp | Val | Asp | Phe | Glu | Ala | Thr | Trp | Asp | Thr | Val |
| | | 195 | | | | | 200 | | | | | 205 | | | |
| Arg | Ser | Ile | Val | Leu | Gln | Lys | Phe | Ala | Gly | Pro | Tyr | Asp | Lys | Gly | Glu |
| | 210 | | | | | 215 | | | | | 220 | | | | |
| Tyr | Ser | Pro | Ser | Val | Gln | Lys | Thr | Leu | Tyr | Asp | Ile | Gln | Val | Leu | Thr |
| 225 | | | | | 230 | | | | | 235 | | | | | 240 |
| Leu | Gly | Gln | Val | Pro | Glu | Ile | Glu | Asp | Met | Glu | Ile | Ser | Leu | Pro | Asn |
| | | | | 245 | | | | | 250 | | | | | 255 | |
| Ile | His | Tyr | Leu | Asn | Ile | Asp | Met | Ser | Lys | Met | Gly | Leu | Ile | Asn | Lys |
| | | | 260 | | | | | 265 | | | | | 270 | | |
| Glu | Glu | Val | Leu | Leu | Pro | Leu | Asp | Asn | Pro | Tyr | Gly | Lys | Ile | Thr | Gly |
| | | 275 | | | | | 280 | | | | | 285 | | | |
| Thr | Val | Lys | Arg | Lys | Leu | Ser | Ser | Arg | Leu | | | | | | |
| | 290 | | | | | 295 | | | | | | | | | |

```
<210> SEQ ID NO 11
<211> LENGTH: 301
<212> TYPE: PRT
<213> ORGANISM: Artificial Sequence
<220> FEATURE:
<223> OTHER INFORMATION: Description of Artificial Sequence:PKS carboxy
      truncated

<400> SEQUENCE: 11
```

| | | | | | | | | | | | | | | | |
|---|---|---|---|---|---|---|---|---|---|---|---|---|---|---|---|
| Met | Ala | His | Tyr | Arg | Asn | Asp | Tyr | Lys | Lys | Asn | Asp | Glu | Val | Glu | Phe |
| 1 | | | | 5 | | | | | 10 | | | | | 15 | |

```
Val Arg Thr Gly Tyr Gly Lys Asp Met Ile Lys Val Leu His Ile Gln
             20                  25                  30

Arg Asp Gly Lys Tyr His Ser Ile Lys Glu Val Ala Thr Ser Val Gln
         35                  40                  45

Leu Thr Leu Ser Ser Lys Lys Asp Tyr Leu His Gly Asp Asn Ser Asp
     50                  55                  60

Val Ile Pro Thr Asp Thr Ile Lys Asn Thr Val Asn Val Leu Ala Lys
 65                  70                  75                  80

Phe Lys Gly Ile Lys Ser Ile Glu Thr Phe Ala Val Thr Ile Cys Glu
                 85                  90                  95

His Phe Leu Ser Ser Phe Lys His Val Ile Arg Ala Gln Val Tyr Val
             100                 105                 110

Glu Glu Val Pro Trp Lys Arg Phe Glu Lys Asn Gly Val Lys His Val
         115                 120                 125

His Ala Phe Ile Tyr Thr Pro Thr Gly Thr His Phe Cys Glu Val Glu
     130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                 165                 170                 175

Gln Phe Thr Thr Leu Pro Glu Val Lys Asp Arg Cys Phe Ala Thr Gln
             180                 185                 190

Val Tyr Cys Lys Trp Arg Tyr His Gln Gly Arg Asp Val Asp Phe Glu
         195                 200                 205

Ala Thr Trp Asp Thr Val Arg Ser Ile Val Leu Gln Lys Phe Ala Gly
     210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
                 245                 250                 255

Glu Ile Ser Leu Pro Asn Ile His Tyr Leu Asn Ile Asp Met Ser Lys
             260                 265                 270

Met Gly Leu Ile Asn Lys Glu Val Leu Leu Pro Leu Asp Asn Pro
         275                 280                 285

Tyr Gly Lys Ile Thr Gly Thr Val Lys Arg Lys Leu Ser
     290                 295                 300

<210> SEQ ID NO 12
<211> LENGTH: 915
<212> TYPE: DNA
<213> ORGANISM: PIG

<400> SEQUENCE: 12
atggctcatt accgtaatga ctacaaaaag aatgatgagg tagagtttgt ccgaactggc      60
tatgggaagg atatgataaa agttctccat attcagcgag atggaaaata tcacagcatt     120
aaagaggtgg caacttcagt gcaactgact ttgagctcca aaaagatta cctgcatgga      180 gacaattcag atgtcatccc tacagacacc atcaagaaca cagttaatgt cctggcgaag     240
ttcaaaggca tcaaaagcat agaaactttt gctgtgacta tctgtgagca tttccttttct    300 tccttcaagc atgtcatcag agctcaagtc tatgtggaag aagttccttg gaagcgtttt     360
gaaaagaatg gagttaagca tgtccatgca tttatttata ctcctactgg aacgcacttc     420
tgtgaggttg aacagataag gaatggacct ccagtcattc attctggaat caaagaccta     480
aaagtcttga aaacaaccca gtctggcttt gaaggattca tcaaggacca gttcaccacc     540
```

```
ctccctgagg tgaaggaccg gtgctttgcc acccaagtgt actgcaaatg gcgctaccac    600
cagggcagag atgtggactt tgaggccacc tgggacactg ttaggagcat tgtcctgcag    660
aaatttgctg ggccctatga caaaggcgag tactcgccct ctgtccagaa gacactctat    720
gacatccagg tgctcaccct gggccaggtt cctgagatag aagatatgga aatcagcctg    780
ccaaatattc actacttaaa catagacatg tccaaaatgg gactgatcaa caaggaagag    840
gtcttgctac ctttagacaa tccatatggc aggattactg gtacagtcaa gaggaagctg    900
acttcaaggc tgtga                                                    915

<210> SEQ ID NO 13
<211> LENGTH: 915
<212> TYPE: DNA
<213> ORGANISM: BABOON

<400> SEQUENCE: 13
atggccgact accataacaa ctataaaaag aatgatgaat tggagtttgt ccgaactggc     60
tatgggaagg atatggtaaa agttctccat attcagcgag atggaaaata tcacagcatt    120
aaagaggtgg caacttcagt gcaacttact ctgagttcca aaaagatta cctgcatgga     180 gataattcag atatcatccc tacagacacc atcaagaaca cagttcatgt cttggcaaag    240
tttaagggaa tcaaaagcat agaagccttt ggtgtgaata tttgtgagta ttttctttct    300
tcttttaacc atgtaatccg agctcaagtc tacgtggaag aaatcccttg gaagcgtctt    360
gaaaagaatg gagttaagca tgtccatgca tttattcaca ctcccactgg aacacacttc    420
tgtgaagttg aacaactgag aagtggaccc ccgtcattc attctggaat caaagacctc    480
aaggtcttga aacaacaca gtctggattt gaaggtttca tcaaggacca gttcaccacc    540
ctccctgagg tgaaggaccg atgctttgcc acccaagtgt actgcaagtg cgctaccac    600 cagtgcaggg atgtggactt cgaggctacc tggggcacca ttcgggacct tgtcctggag    660
aaatttgctg ggccctatga caaaggcgag tactcaccct ctgtgcagaa gaccctctat    720
gatatccagg tgctctccct gagccgagtt cctgagatag aagatatgga aatcagcctg    780
ccaaacattc actacttcaa tatagacatg tccaaaatgg gtctgatcaa caaggaagag    840
gtcttgctgc cattagacaa tccatatgga aaaattactg gtacagtcaa gaggaagttg    900
tcttcaagac tgtga                                                    915
```